US009895185B2

(12) United States Patent
Hoey et al.

(10) Patent No.: US 9,895,185 B2
(45) Date of Patent: Feb. 20, 2018

(54) SYSTEMS AND METHODS FOR PROSTATE TREATMENT

(75) Inventors: Michael Hoey, Shoreview, MN (US); Mark Schrom, Forest Lake, MN (US); Stephanos Paulos, Little Canada, MN (US); Randall Beyreis, Corcoran, MN (US); Mark Bilitz, Plymouth, MN (US)

(73) Assignee: NXTHERA, INC., Maple Grove, MN (US)

( * ) Notice: Subject to any disclaimer, the term of this patent is extended or adjusted under 35 U.S.C. 154(b) by 1006 days.

(21) Appl. No.: 14/241,977

(22) PCT Filed: Sep. 13, 2012

(86) PCT No.: PCT/US2012/055164
§ 371 (c)(1),
(2), (4) Date: Jun. 10, 2014

(87) PCT Pub. No.: WO2013/040209
PCT Pub. Date: Mar. 21, 2013

(65) Prior Publication Data
US 2014/0288543 A1 Sep. 25, 2014

Related U.S. Application Data

(60) Provisional application No. 61/534,053, filed on Sep. 13, 2011.

(51) Int. Cl.
*A61B 18/18* (2006.01)
*A61B 18/04* (2006.01)
*A61B 18/14* (2006.01)
*A61B 18/00* (2006.01)

(52) U.S. Cl.
CPC .......... *A61B 18/04* (2013.01); *A61B 18/1492* (2013.01); *A61B 2018/00029* (2013.01);
(Continued)

(58) Field of Classification Search
CPC .......... A61B 18/04; A61B 2018/00547; A61B 2018/048; A61B 2218/002;
(Continued)

(56) References Cited

U.S. PATENT DOCUMENTS

| 408,899 A | 8/1889 | Small |
| 1,719,750 A | 7/1929 | Bridge et al. |
| 4,672,963 A | 6/1987 | Barken |
| 4,920,982 A | 5/1990 | Goldstein |
| 4,950,267 A | 8/1990 | Ishihara et al. |

(Continued)

FOREIGN PATENT DOCUMENTS

| CN | 2061443 U | 9/1990 |
| CN | 2418844 Y | 2/2001 |

(Continued)

OTHER PUBLICATIONS

US 5,326,343, 07/1994, Rudie et al. (withdrawn)
Hoey et al.; U.S. Appl. No. 14/773,853 entitled "Systems and methods for treating prostate cancer," filed Sep. 9, 2015.
(Continued)

*Primary Examiner* — Michael Peffley
*Assistant Examiner* — Amanda Zink
(74) *Attorney, Agent, or Firm* — Shay Glenn LLP

(57) ABSTRACT

A vapor delivery needle is provided that may include any of a number of features. One feature of the energy delivery probe is that it can apply condensable vapor energy to tissue, such as a prostrate, to shrink, damage, denaturate the prostate. In some embodiments, the vapor delivery needle can be advanced a pre-determined distance into the prostate by an actuation mechanism. The actuation mechanism can comprise, for example, a spring, or at least one magnet. Methods associated with use of the energy delivery probe are also covered.

39 Claims, 27 Drawing Sheets

(52) U.S. Cl.
CPC ............. *A61B 2018/00517* (2013.01); *A61B 2018/00547* (2013.01); *A61B 2018/00577* (2013.01); *A61B 2018/00642* (2013.01); *A61B 2018/00678* (2013.01); *A61B 2018/00744* (2013.01); *A61B 2018/00791* (2013.01); *A61B 2018/00821* (2013.01); *A61B 2018/048* (2013.01); *A61B 2218/002* (2013.01); *A61B 2218/007* (2013.01)

(58) Field of Classification Search
CPC .......... A61B 2218/007; A61B 18/1492; A61B 2018/00029; A61B 2018/00035; A61B 2018/00517; A61B 2018/00577; A61B 2018/00642; A61B 2018/00678; A61B 2018/00744; A61B 2018/00791
See application file for complete search history.

(56) References Cited

U.S. PATENT DOCUMENTS

| | | |
|---|---|---|
| 5,117,482 A | 5/1992 | Hauber |
| 5,222,185 A | 6/1993 | McCord, Jr. |
| 5,300,099 A | 4/1994 | Rudie |
| 5,312,399 A | 5/1994 | Hakky et al. |
| 5,330,518 A | 7/1994 | Neilson et al. |
| 5,366,490 A | 11/1994 | Edwards et al. |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thome et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thome et al. |
| 5,871,481 A | 2/1999 | Kannenberg et al. |
| 5,873,877 A | 2/1999 | McGaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Muller et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | McGovern et al. |
| 6,494,902 B2 | 12/2002 | Hoey et al. |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |
| 6,638,275 B1 | 10/2003 | McGaffigan et al. |
| 6,640,139 B1 | 10/2003 | Ueberle |
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 | 7/2004 | Hoey et al. |
| 6,780,178 B2 | 8/2004 | Palanker et al. |
| 6,827,718 B2 | 12/2004 | Hutchins et al. |
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |

(56) References Cited

U.S. PATENT DOCUMENTS

| | | | |
|---|---|---|---|
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chornenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,900,223 B2 | 12/2014 | Shadduck |
| 2002/0078956 A1 | 6/2002 | Sharpe et al. |
| 2002/0111617 A1 | 8/2002 | Cosman et al. |
| 2002/0177846 A1 | 11/2002 | Mulier et al. |
| 2003/0069575 A1 | 4/2003 | Chin et al. |
| 2003/0092689 A1 | 5/2003 | Escandon et al. |
| 2003/0097126 A1 | 5/2003 | Woloszko |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1* | 12/2008 | Shachar ............... A61B 5/06 335/234 |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0286679 A1* | 11/2010 | Hoey ............... A61B 18/04 606/27 |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0160648 A1 | 6/2011 | Hoey |
| 2011/0264176 A1 | 10/2011 | Jackson et al. |
| 2011/0319759 A1 | 12/2011 | Liu et al. |
| 2012/0259271 A1 | 10/2012 | Shadduck et al. |
| 2012/0265276 A1 | 10/2012 | Curley |
| 2012/0323167 A1 | 12/2012 | Hoey et al. |
| 2013/0006231 A1 | 1/2013 | Sharma et al. |
| 2013/0066308 A1 | 3/2013 | Landman |
| 2013/0072855 A1 | 3/2013 | Sherry et al. |
| 2013/0074847 A1 | 3/2013 | Hoey et al. |
| 2013/0158534 A1 | 6/2013 | Hoey et al. |
| 2013/0172867 A1 | 7/2013 | Shadduck et al. |
| 2013/0261692 A1 | 10/2013 | Cardinal et al. |
| 2014/0039356 A1 | 2/2014 | Sachs et al. |
| 2014/0107637 A1 | 4/2014 | Hoey et al. |
| 2014/0200568 A1 | 7/2014 | Sharma |
| 2015/0126990 A1 | 5/2015 | Sharma et al. |
| 2015/0157384 A1 | 6/2015 | Hoey et al. |
| 2016/0081736 A1 | 3/2016 | Hoey et al. |
| 2017/0056089 A1 | 3/2017 | Hoey et al. |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| CN | 101803947 A | 8/2010 |
| JP | 7-507696 A | 8/1995 |
| JP | 8-501957 A | 3/1996 |
| JP | 8-504613 A | 5/1996 |
| JP | 11-318925 A | 11/1999 |
| JP | 200014663 A | 1/2000 |
| JP | 2000005191 A | 1/2000 |
| JP | 2001500763 A | 1/2001 |

(56) References Cited

FOREIGN PATENT DOCUMENTS

| JP | 2005137916 A | 6/2005 |
|----|----|----|
| WO | WO 92/10142 A1 | 6/1992 |
| WO | WO 01/24715 A1 | 4/2001 |
| WO | WO 03/088851 A1 | 10/2003 |
| WO | WO 03/096871 A2 | 11/2003 |
| WO | WO 2006/004482 A1 | 1/2006 |
| WO | WO 2008/083407 A1 | 7/2008 |
| WO | WO2010/080467 A2 | 7/2010 |
| WO | WO 2013/160772 A2 | 10/2013 |
| WO | WO2015/089190 A1 | 6/2015 |

OTHER PUBLICATIONS

Hoey et al.; U.S. Appl. No. 14/453,254 entitled "Systems and Methods for Treatment of BPH," filed Aug. 6, 2014.

Hoey et al.; U.S. Appl. No. 14/384,774 entitled "Induction coil vapor generator," filed Sep. 12, 2014.

Hai; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pcricms/node/233 on May 10, 2012; 4 pages.

Hastings et al.; U.S. Appl. No. 15/011,005 entitled "Vapor ablation systems and methods," filed Jan. 29, 2016.

Hastings et al.; U.S. Appl. No. 15/035,944 entitled "Vapor ablation systems and methods," filed May 11, 2016.

Hoey et al.; U.S. Appl. No. 15/154,536 entitled "Systems and methods for treating the bladder with condensable vapor," filed May 13, 2016.

\* cited by examiner

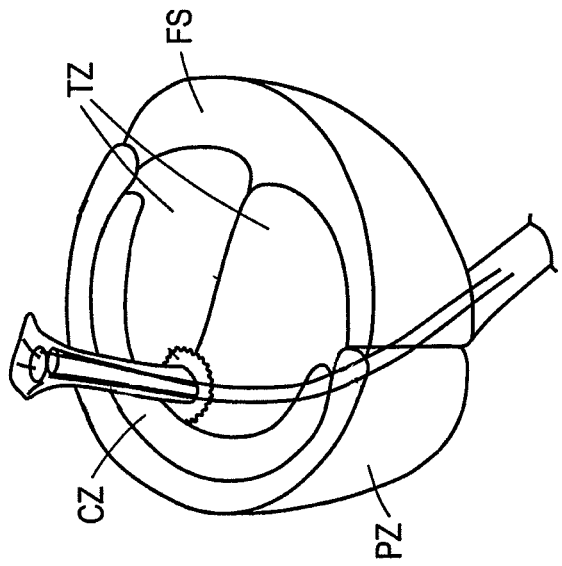
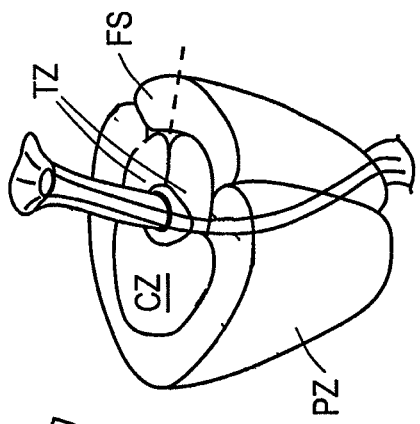
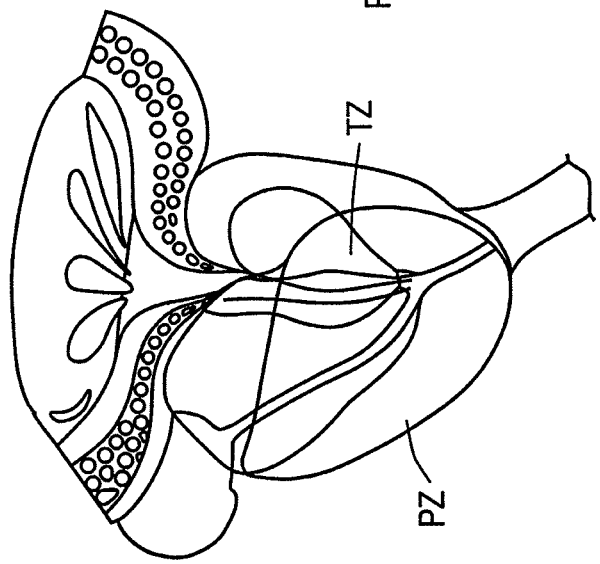
FIG. 2C
FIG. 2B
FIG. 2A

SYSTEMS AND METHODS FOR PROSTATE TREATMENT

CROSS REFERENCE TO RELATED APPLICATIONS

This application is the national stage under 35 USC 371 of International Application No. PCT/US2012/055164, filed Sep. 13, 2012, which application claims the benefit of U.S. Provisional Application No. 61/534,053, filed Sep. 13, 2011.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

The present invention relates to devices and related methods for treatment of benign prostatic hyperplasia using a minimally invasive approach.

BACKGROUND

Benign prostatic hyperplasia (BPH) is a common disorder in middle-aged and older men, with prevalence increasing with age. At age 50, more than one-half of men have symptomatic BPH, and by age 70, nearly 90% of men have microscopic evidence of an enlarged prostate. The severity of symptoms also increase with age with 27% of patients in the 60-70 age bracket having moderate-to-severe symptoms, and 37% of patients in their 70's suffering from moderate-to-severe symptoms.

The prostate early in life is the size and shape of a walnut and prior to the enlargement resulting from BPH, weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra, thus causing resistance to urine flow.

FIG. 1 is a sectional schematic view the male urogenital anatomy, with the walnut-sized prostate gland 100 located below the bladder 105 and bladder neck indicated at 106. The walls 108 of bladder 105 can expand and contract to cause urine flow through the urethra 110, which extends from the bladder 105, through the prostate 100 and penis 112. The portion of urethra 110 that is surrounded by the prostate gland 100 is referred to as the prostatic urethra 120. The prostate 100 also surrounds the ejaculatory ducts 122 which have an open termination in the prostatic urethra 120. During sexual arousal, sperm is transported from the testes 124 by the ductus deferens 126 to the prostate 100 which provides fluids that combine with sperm to form semen during ejaculation. On each side of the prostate, the ductus deferens 126 and seminal vesicles 128 join to form a single tube called an ejaculatory duct 122. Thus, each ejaculatory duct 122 carries the seminal vesicle secretions and sperm into the prostatic urethra 120.

Referring to FIGS. 2A-2C, the prostate glandular structure can be classified into three zones: the peripheral zone, transition zone, and central zone. The peripheral zone PZ, which is the region forming the postero-inferior aspect of the gland, contains 70% of the prostate glandular elements in a normal prostate (FIGS. 2A-2C). A majority of prostate cancers (up to 80%) arise in the peripheral zone PZ. The central zone CZ surrounds the ejaculatory ducts 122 and contains about 20-25% of the prostate volume. The central zone is often the site of inflammatory processes. The transition zone TZ is the site in which benign prostatic hyperplasia develops, and contains about 5-10% of the volume of glandular elements in a normal prostate (FIG. 2C), but can constitute up to 80% of such volume in cases of BPH. The transition zone TZ consists of two lateral prostate lobes and the periurethral gland region indicated at 130. As can be understood from FIGS. 2A-2C, there are natural barriers around the transition zone TZ, i.e., the prostatic urethra 120, the anterior fibromuscular stroma FS, and a fibrous plane FP between the transition zone TZ and peripheral zone PZ. In FIGS. 2A-2C, the anterior fibromuscular stroma FS or fibromuscular zone can be seen and is predominantly fibromuscular tissue.

BPH is typically diagnosed when the patient seeks medical treatment complaining of bothersome urinary difficulties. The predominant symptoms of BPH are an increase in frequency and urgency of urination, and a significant decrease in the rate of flow during urination. BPH can also cause urinary retention in the bladder which in turn can lead to lower urinary tract infection (LUTI). In many cases, the LUTI then can ascend into the kidneys and cause chronic pyelonephritis, and can eventually lead to renal insufficiency. BPH also may lead to sexual dysfunction related to sleep disturbance or psychological anxiety caused by severe urinary difficulties. Thus, BPH can significantly alter the quality of life with aging of the male population.

BPH is the result of an imbalance between the continuous production and natural death (apoptosis) of the glandular cells of the prostate. The overproduction of such cells leads to increased prostate size, most significantly in the transition zone which traverses the prostatic urethra.

In early stage cases of BPH, pharmacological treatments can alleviate some of the symptoms. For example, alpha-blockers treat BPH by relaxing smooth muscle tissue found in the prostate and the bladder neck, which may allow urine to flow out of the bladder more easily. Such drugs can prove effective until the glandular elements cause overwhelming cell growth in the prostate.

More advanced stages of BPH, however, can only be treated by surgical or less-invasive thermal ablation device interventions. A number of methods have been developed using electrosurgical or mechanical extraction of tissue, and thermal ablation or cryoablation of intracapsular prostatic tissue. In many cases, such interventions provide only transient relief, and these treatments often cause significant peri-operative discomfort and morbidity.

In a prior art thermal ablation method, RF energy is delivered to prostate tissue as schematically depicted in FIGS. 3A-3B. FIG. 3A depicts the elongated prior art RF needle being penetrated into a plurality of locations in a prostate lobe. In a first aspect of the prior art method, the elongated RF needle typically is about 20 mm in length, together with an insulator that penetrates into the lobe. The resulting RF treatment thus ablates tissue away from the prostatic urethra 120 and does not target tissue close to, and parallel to, the prostatic urethra 120. In another aspect of the prior art RF thermal ablation method, the application of RF energy typically extends for 1 to 3 minutes or longer which allows thermal diffusion of the RF energy to ablate tissue out to the capsule periphery. Such prior art RF energy delivery methods may not create a durable effect, since smooth muscle tissue and alpha adrenergic receptors are not uniformly ablated around the prostatic urethra or within the transition zone. As a result, tissue in the prostate lobes can continue to grow and impinge on the urethra thus limiting long-term effectiveness of the treatment.

SUMMARY OF THE DISCLOSURE

According to the embodiments described above, a prostate treatment device can be provided comprising an introducer shaft sized and configured for transurethral access into a patient, a vapor generator configured to generate a condensable vapor, a vapor delivery needle in communication with the vapor generator and slidably disposed within the introducer shaft, and a magnetic actuator configured to apply magnetic force to the vapor delivery needle to move the vapor delivery needle between a retracted position inside the introducer shaft and an extended position at least partially outside of the introducer shaft.

In some embodiments, the magnetic actuator is configured to axially move the vapor delivery needle toward the extended position from the retracted position at a velocity ranging from 0.1 meter per second to 20.0 meters per second. In another embodiment, the vapor delivery needle can move between the retracted and extended positions (and vice versa) at a velocity ranging from 1 meter per second to 5 meters per second.

In other embodiments, the magnetic actuator is configured to cause a tip portion of the vapor delivery needle to penetrate into prostate tissue when moving toward the extended position from the retracted position. In some embodiments, the vapor delivery needle is sized and configured to extend into prostate tissue when the introducer shaft is positioned within a urethra of the patient.

In one embodiment, the magnetic actuator further comprises a first magnet carried by the vapor delivery needle, wherein the magnetic actuator is configured to move the first magnet and the vapor delivery needle proximally and distally along a longitudinal axis of the introducer shaft. In another embodiment, the magnetic actuator further comprises a second magnet carried in a frame of a handle of the device, the second magnet being configured to interact with the first magnet to move the vapor delivery needle proximally and distally along the longitudinal axis of the introducer shaft. In some embodiments, the frame is rotatable in the handle. In yet another embodiment, the magnetic actuator further comprises a third magnet carried in a second frame of the handle, the third magnet being configured to interact with the first and second magnets to move the vapor delivery needle proximally and distally along the longitudinal axis of the introducer shaft.

In some embodiments, the device can further include a grip adapted for manual control of the magnetic actuator to move the vapor delivery needle between the retracted position and the extended position. In another embodiment, the device comprises a gear rack coupled to the grip, the gear rack being configured to rotate the frame and the second magnet so as to engage or disengage from the first magnet.

In some embodiments, the device can comprise a lock configured to lock the vapor delivery needle in the retracted position. The device can further comprise a trigger adapted to release the lock to thereby move the vapor delivery needle to the extended position from the retracted position.

In one embodiment, the magnetic actuator is configured to apply a suitable magnetic force to cause the tip portion of the vapor delivery needle to withdraw from prostate tissue when moving to the retracted position. In some embodiments, the suitable magnetic force can range from 1 to 3 pounds of force during advancement and retraction. In one embodiment, the force can be at least 2 pounds of force.

In some embodiments, the device can further include a vapor actuator for actuating a flow of condensable vapor through the vapor delivery needle. The device can further comprise an interlock mechanism which permits actuation of the vapor actuator only if a releasable lock has been released.

In some embodiments, the magnetic actuator comprises at least one rare earth magnet. In other embodiments, the magnetic actuator comprises at least one neodymium or neodymium-iron-boron magnet.

In one embodiment, the magnetic actuator orients first and second magnets relative to one another to utilize repelling forces to move the vapor delivery needle along a longitudinal axis of the introducer shaft. In another embodiment, the magnetic actuator orients first and second magnets relative to one another to utilize attracting forces to move the vapor delivery needle along a longitudinal axis of the introducer shaft. In some embodiments, the magnetic actuator orients first and second magnets relative to one another to utilize attracting and repelling forces to move the vapor delivery needle along a longitudinal axis of the introducer shaft.

A method of treating prostate tissue is also provided, comprising inserting a shaft of a prostate therapy device transurethrally until a working end of the shaft is proximate to the prostate tissue, actuating a magnetic assembly to advance a vapor delivery needle from the introducer into the prostate tissue, and delivering condensable vapor from the vapor delivery needle into the prostate tissue.

In some embodiments, the condensable vapor provides a thermal effect in the prostate tissue.

In one embodiment, the vapor delivery needle advances into the prostate tissue under the influence of repelling forces between first and second magnets of the magnetic assembly. In another embodiment, the vapor delivery needle advances into the prostate tissue under the influence of attracting forces between first and second magnets of the magnetic assembly. In some embodiments, the vapor delivery needle advances into the prostate tissue under the influence of attracting and repelling forces between first and second magnets of the magnetic assembly.

A prostate treatment device is also provided, comprising an introducer shaft sized and configured for transurethral access into a patient, a vapor generator configured to generate a condensable vapor, a vapor delivery needle in communication with the vapor generator and slidably disposed within the introducer shaft, and an actuation mechanism configured to apply force to move a distal portion of the vapor delivery needle from a retracted position inside the introducer shaft to an extended position outside of the introducer shaft.

In some embodiments, the actuation mechanism moves a distal tip of the vapor delivery needle outward from the introducer shaft a distance of less than 2 cm.

In another embodiment, the device comprises a controller configured to deliver a selected volume of condensable vapor through the needle that carries less than 240 calories of energy.

In some embodiments, the actuation mechanism comprises a spring. In other embodiments, the actuation mechanism comprises at least one magnet. In one embodiment, the actuation mechanism is configured to move the vapor delivery needle toward the extended position from the retracted position at a velocity ranging from 0.1 meter per second to 20.0 meters per second.

In one embodiment, the vapor delivery needle is sized and configured to extend into prostate tissue when the introducer shaft is positioned within a urethra of the patient.

In some embodiments, the actuation mechanism comprises a first magnet carried by the vapor delivery needle. In another embodiment, the actuation mechanism comprises a second magnet carried in a frame of a handle of the device, the second magnet being configured to interact with the first magnet to move the vapor delivery needle. In some embodiments, the frame is rotatable in the handle.

In some embodiments, the device can further include a grip adapted for manual control of the magnetic actuator to move the vapor delivery needle between the retracted position and the extended position. In another embodiment, the device comprises a gear rack coupled to the grip, the gear rack being configured to rotate the frame and the second magnet so as to engage or disengage from the first magnet.

In some embodiments, the device can comprise a lock configured to lock the vapor delivery needle in the retracted position. The device can further comprise a trigger adapted to release the lock to thereby move the vapor delivery needle to the extended position from the retracted position.

In some embodiments, the device can further include a vapor actuator for actuating a flow of condensable vapor through the vapor delivery needle. The device can further comprise an interlock mechanism which permits actuation of the vapor actuator only if a releasable lock has been released.

A method of treating prostate tissue is provided, comprising inserting a shaft of a prostate therapy device transurethrally until a working end of the shaft is proximate to the prostate tissue, advancing a vapor delivery needle from the introducer into at least one site in prostate tissue to a depth of less than 2 cm, and delivering condensable vapor from the vapor delivery needle into the prostate tissue.

In some embodiments, the condensable vapor provides a thermal effect in the prostate tissue. In other embodiments, the condensable vapor delivers less than 240 calories of energy at each site.

In one embodiment, the vapor delivery needle advances into the prostate tissue under forces applied by a spring. In another embodiment, the vapor delivery needle advances into the prostate tissue under the influence of at least one magnet.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIGS. 2A-2C are views of a patient's prostate showing zones of prostate tissue.

DETAILED DESCRIPTION OF THE INVENTION

In general, one method of the invention for treating BPH comprises introducing a heated vapor interstitially into the interior of a prostate, wherein the vapor controllably ablates prostate tissue. This method can utilize vapor for applied thermal energy of between 50 calories and 300 calories per each individual vapor treatment (and assumes multiple treatments for each prostate lobe) in an office-based procedure. The method can cause localized ablation of prostate tissue, and more particularly the applied thermal energy from vapor can be localized to ablate tissue adjacent the urethra without damaging prostate tissue that is not adjacent the urethra.

The present invention is directed to the treatment of BPH, and more particularly for ablating transitional zone prostate tissue without ablating central or peripheral zone prostate tissue.

In one embodiment, the present invention is directed to treating a prostate using convective heating in a region adjacent the prostatic urethra.

In one embodiment, the method of ablative treatment is configured to target smooth muscle tissue, alpha adrenergic receptors, sympathetic nerve structures and vasculature parallel to the prostatic urethra between the bladder neck region and the verumontanum region to a depth of less than 2 cm.

In one embodiment, the system includes a vapor delivery mechanism that delivers vapor media, including vapor media. The system can utilize a vapor source configured to provide vapor having a temperature of at least 60° C., 80° C., 100° C., 120° C., or 140° C.

In another embodiment, the system further comprises a computer controller configured to deliver vapor for an interval ranging from 1 second to 30 seconds.

In another embodiment, the system further comprises a source of a pharmacologic agent or other chemical agent or compound for delivery with the vapor. These agents include, without limitation, an anesthetic, an antibiotic or a toxin such as Botox®, or a chemical agent that can treat cancerous tissue cells. The agent also can be a sealant, an adhesive, a glue, a superglue or the like.

Another method of the invention provides a treatment for BPH that can use a transrectal or transperineal approach using a transrectal ultrasound system (TRUS) as an imaging means to image the prostate, and navigate a vapor delivery tool to the targeted treatment sites.

In another method of the invention, the tool or vapor delivery needle working end can be advanced manually or at least in part by a spring mechanism.

In another aspect of the invention, the system may contemporaneously deliver cooling fluids to the urethra during an ablation treatment to protect the interior lining of the urethra.

Figure 4:
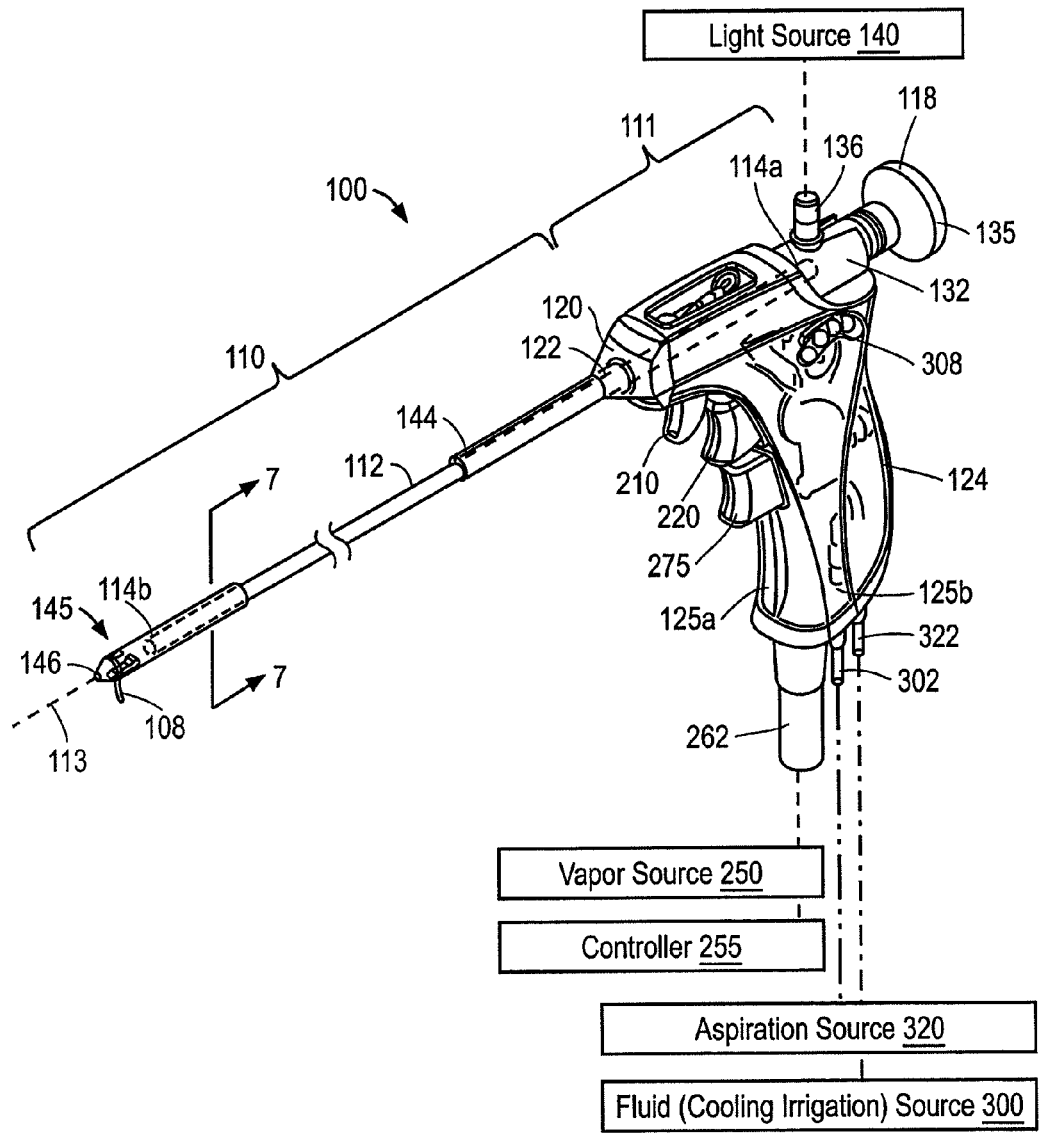
FIG. 4 is a perspective view of a probe corresponding to the invention.
Figure 5:
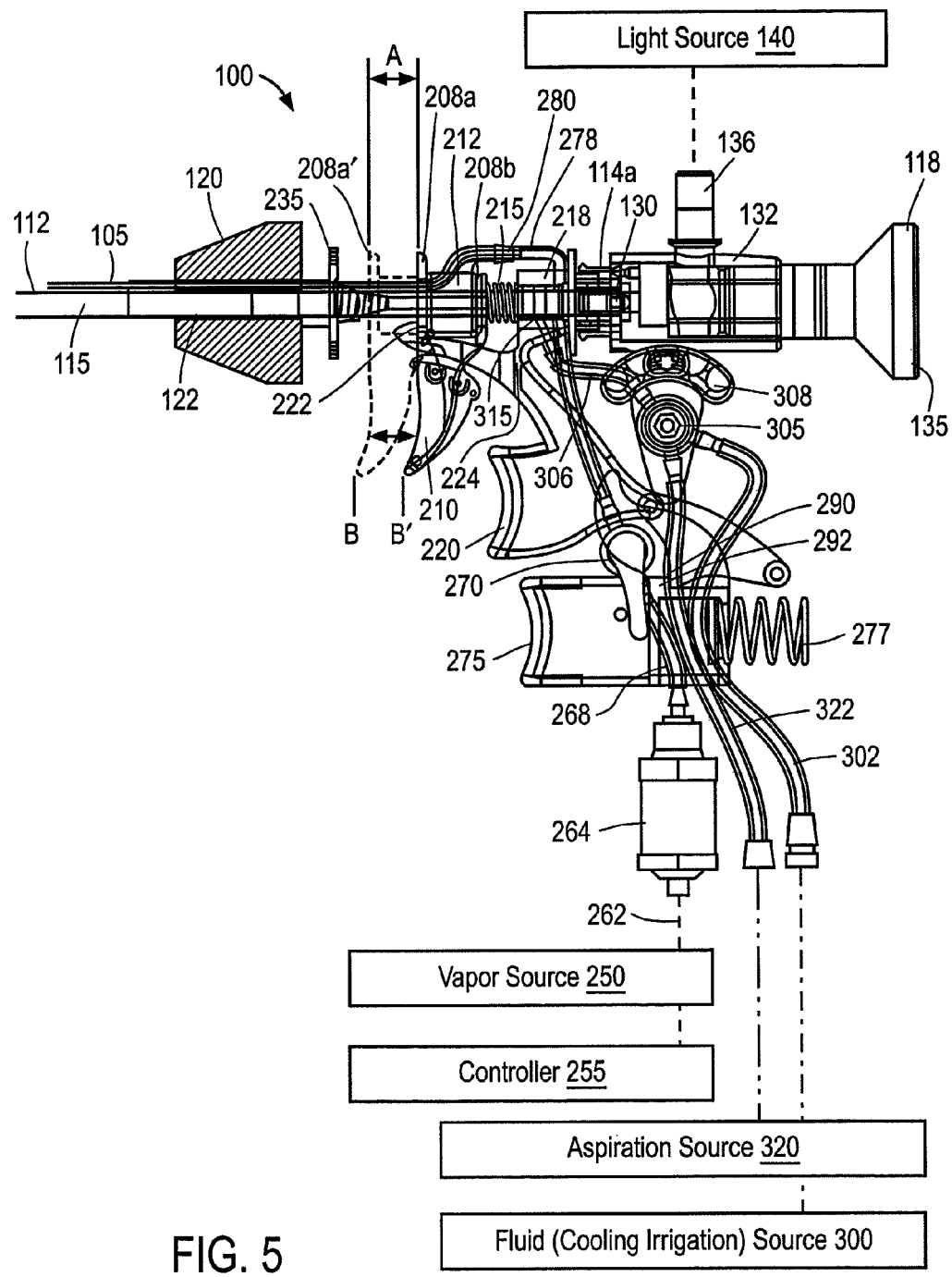
FIG. 5 is a view of components within a handle portion of the probe of FIG. 4.
Figure 6:
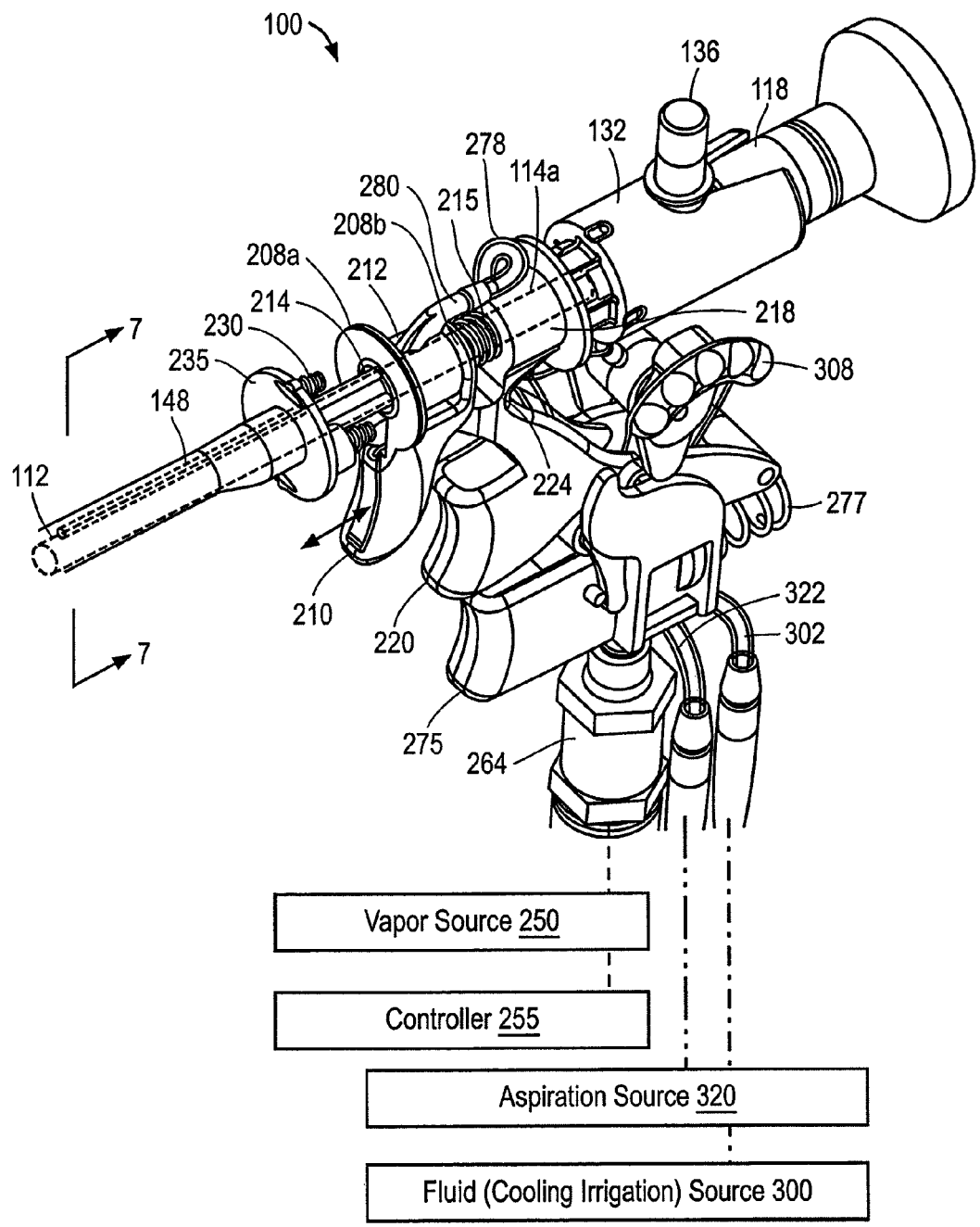
FIG. 6 is another view of components within a handle portion of the probe of FIG. 4.

FIGS. 4, 5 and 6 depict one embodiment of probe 100 of the system of the invention that is adapted for trans-urethral access to the prostate and which provides viewing means to view the urethra as the probe is navigated to a site in the interior of the patient's prostate. The probe 100 further carries an extendable and retractable microcatheter member 105 (FIGS. 5-6) having a distal tip portion 108 (FIG. 4) that can be penetrated into precise targeted locations in prostate lobes to ablate targeted tissue volumes.

Handle and Introducer Portion

In FIG. 4, it can be seen that probe 100 has an elongate introducer portion 110 for insertion into the urethra and a handle portion 111 for gripping with a human hand. The key structural component of introducer portion 110 comprises a rigid introducer sleeve or extension sleeve 112 extending along longitudinal axis 113 with proximal end 114a and distal end 114b. The bore 115 in the rigid extension sleeve extends along longitudinal axis 116. In one embodiment, referring to FIGS. 4 and 5, the extension sleeve 112 comprises a thin-wall stainless steel tube with bore 115 dimensioned to receive a commercially available viewing scope or endoscope 118. The schematic cut-away view of FIG. 5 shows structural bulkhead 120 coupled to a medial portion 122 of extension sleeve 112. The structure or bulkhead 120 comprises the structural member to which the molded handle having pistol grip 124, and more particularly the right- and left-side mating handle parts, 125a and 125b, are coupled (FIG. 4). The bulkhead can be a plastic molded part that can be fixed to sleeve 112 or rotationally coupled to sleeve 112.

Figure 7:
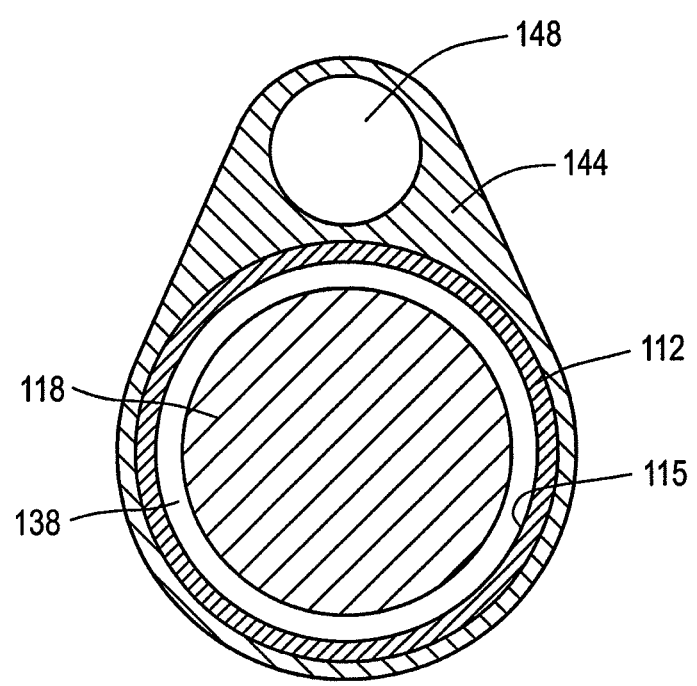
FIG. 7 is a cross sectional view of a probe.

Referring to FIGS. 5-6, in which the molded handle left and right sides are not shown, it can be seen that bore 115 in sleeve 112 has a proximal open end 130 into which the endoscope 118 can be inserted. The proximal end portion 114a of extension sleeve 112 is coupled to an adapter mechanism 132 that releasably engages the endoscope 118 and rotationally aligns the scope 118 with the introducer portion 110. The endoscope 118 has a proximal viewing end 135 and light connector 136 extending outward from the viewing end 136 for coupling a light source 140 to the endoscope. FIG. 7 illustrates that bore 115 in sleeve 112 has a diameter ranging from about 2 to 5 mm for accommodating various endoscopes 118, while at the same time providing an annular space 138 for allowing an irrigation fluid to flow through bore 115 and outwardly from the introducer portion.

Figure 8:
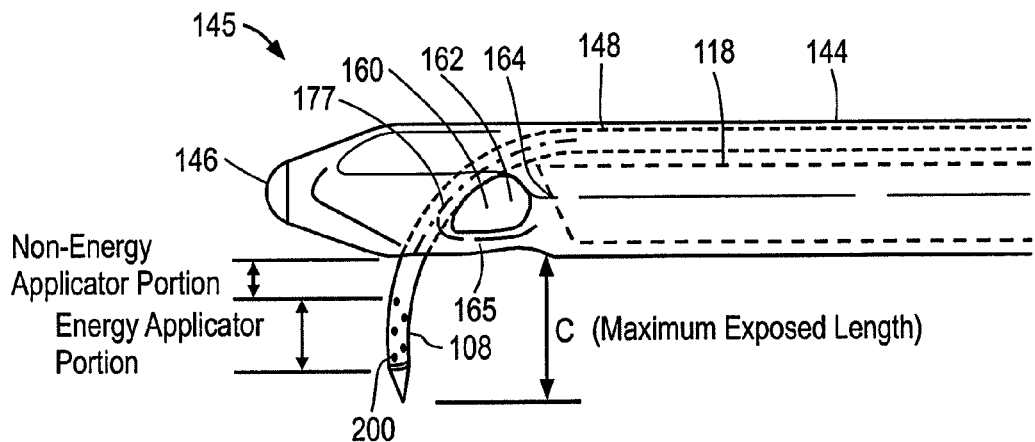
FIG. 8 is a side view of a microcatheter or needle of a probe.
Figure 9:
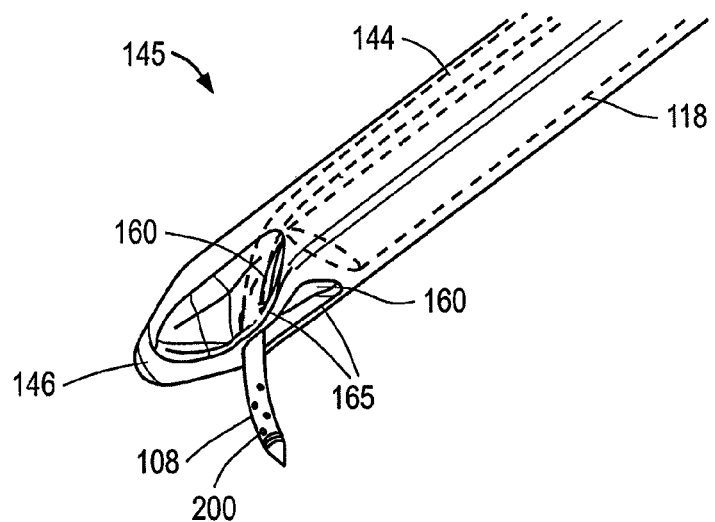
FIG. 9 is a side elevation view of the microcatheter or a vapor delivery needle of the probe of FIG. 4 showing its dimensions and vapor outlets.

In one embodiment of system 100, referring to FIGS. 5-8, the extendable-retractable microcatheter 105 comprises a thin-wall flexible polymer tube with a sharp tip that is axially slidable in a passageway 148 in the introducer portion 110. FIGS. 4, 7 and 9 show that the introducer portion 110 comprises an elongate introducer body 144 of plastic or another suitable material that surrounds extension sleeve 112. The introducer body 144 extends to a distal working end portion 145 having a blunt nose or tip 146 for advancing through the urethra. The elongate introducer body 144 is further configured with passageway 148 that accommodates the microcatheter member 105 as will be described below. Referring to FIGS. 8-9, the distal end portion 145 of the introducer body 144 is configured with openings 160 that open to central open region 162 that is distal to the distal lens 164 of endoscope 118 that allows for viewing of the urethra through the lens 164 of the endoscope during navigation. The endoscope 118 can have a lens with a 30°, 12.5° or other angle for viewing through openings 160. As can be seen in FIGS. 8-9, the openings 160 have bridge elements 165 therebetween that function to prevent tissue from falling into central open region 162 of the introducer body 144. In FIG. 8, it can be seen that the working end portion 105 of the flexible microcatheter shaft 105 is disposed adjacent to open region 162 and thus can be viewed through the endoscope lens 164.

Microcatheter and Spring-Actuator

Figure 1:
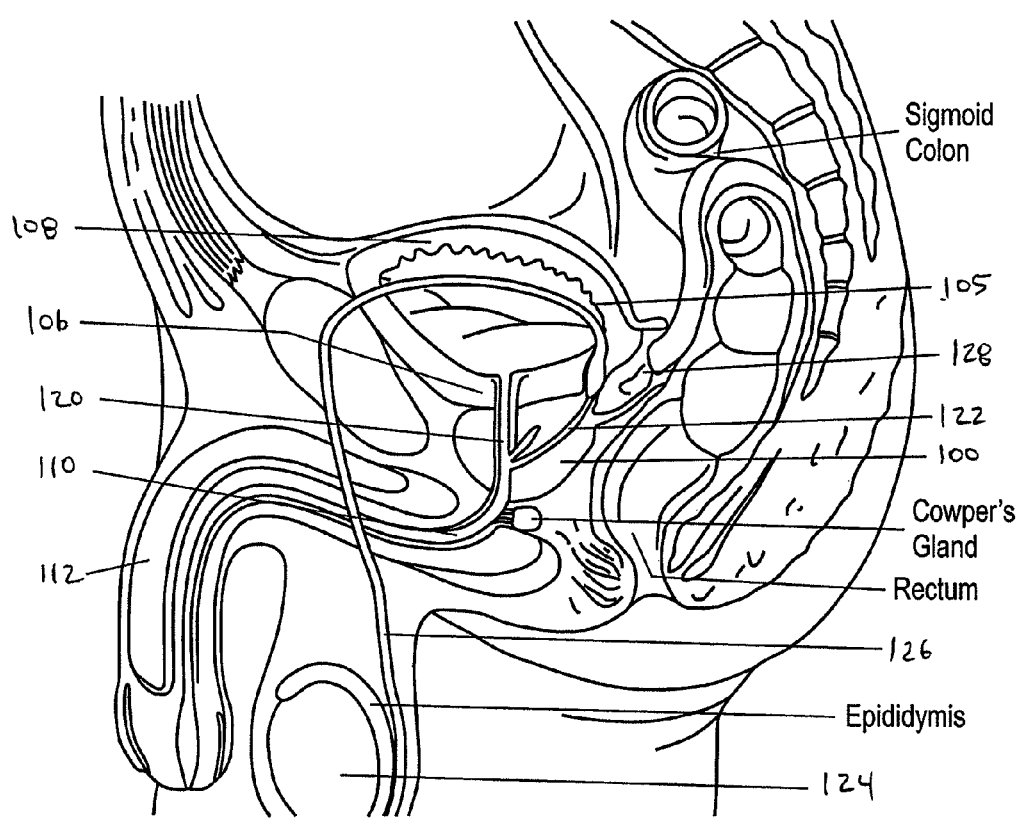
FIG. 1 is a sectional schematic view the male urogenital anatomy.
Figure 10:
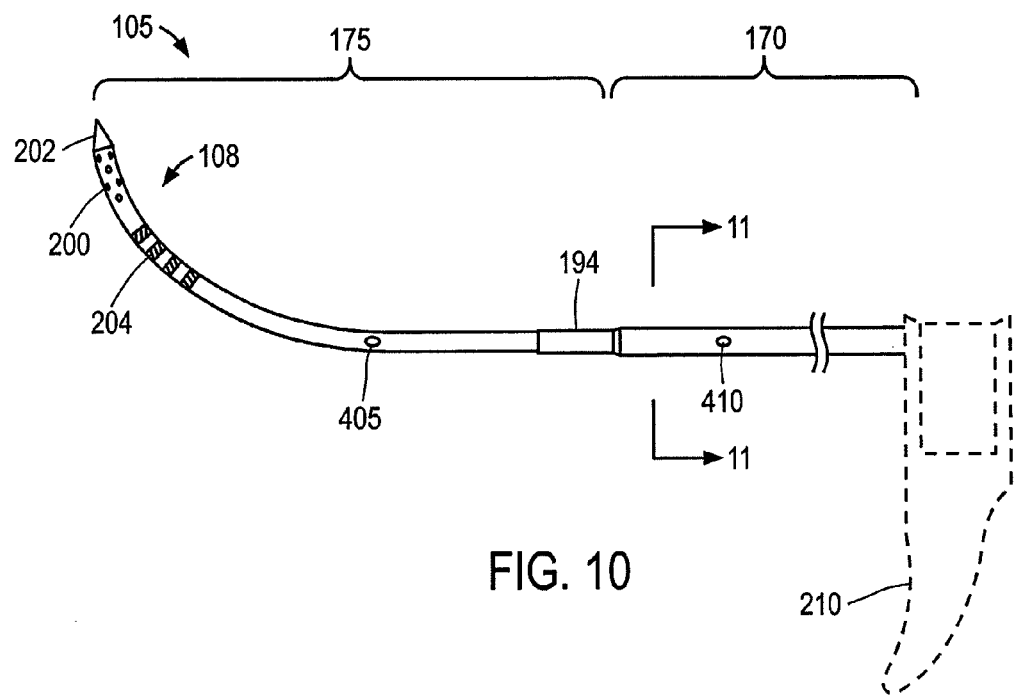
FIG. 10 is another view of the microcatheter of FIG. 9.
Figure 11:
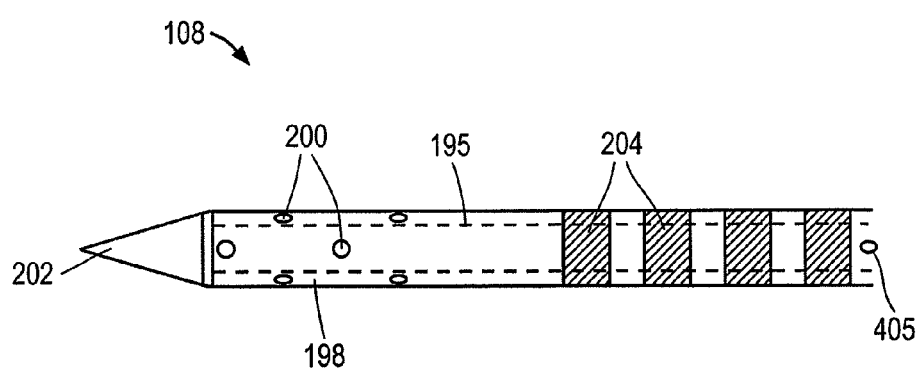
FIG. 11 is another view of a distal portion of the microcatheter of FIG. 10.
Figure 12:
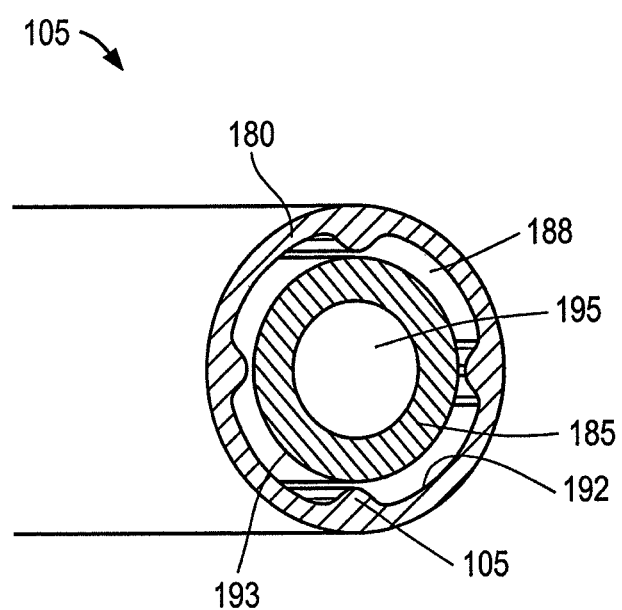
FIG. 12 is a sectional view of the microcatheter of FIG. 10 taken along line 11-11 of FIG. 10.

FIGS. 10-11 show the flexible microcatheter member or needle 105 de-mated from the probe 100 to indicate its repose shape. In one embodiment, the microcatheter 105 has a first (proximal) larger cross-section portion 170 that necks down to second (distal) cross-section portion 175 wherein the smaller cross-section portion 175 has a curved repose shape with the curve configured to conform without significant resistance to the contour of the curved axis 177 of the path followed by the working end 108 of the microcatheter 105 as it is moved from its non-extended position to its extended position as shown in FIGS. 1, 8 and 9. In one embodiment, referring to FIGS. 10-12, the microcatheter's first cross section portion 170 comprises a thin wall outer sleeve 180 that is concentrically outward from inner microcatheter tube 185 that extends the length of the microcatheter member 105. As can be seen in FIG. 12, the outer sleeve 180 provides a thermally insulative air gap 188 around inner tubular member 185. In one embodiment shown depicted in FIG. 12, the outer sleeve 180 is configured with intermittent protrusions 190 that maintain the air gap 188 between the inner surface 192 of outer sleeve 180 and outer surface 193 of inner microcatheter tube. FIG. 9 shows that the outer sleeve 180 has necked down portion 194 that is bonded to inner microcatheter tube 185 by any suitable means such as ultrasonic bonding, adhesives or the like. Referring back to FIG. 10, both the outer sleeve 180 and inner tubular member can comprise a high-temperature resistant polymer such as Ultem® that is suited for delivering a high temperature vapor as will be described below. In one embodiment, the microcatheter tube 185 has an outside diameter of 0.050" with an interior lumen 195 of approximately 0.030". Referring to FIGS. 8-9, one embodiment of working end portion 108 for delivering vapor media to tissue has a thin wall 198 with a plurality of outlet ports 200 therein that are configured for emitting a vapor media into tissue as will be described below. The outlet ports can range in number from about 2 to 100, and in one embodiment consist of 12 outlets each having a diameter of 0.008" in six rows of two outlets with the rows staggered around the working end 108 as shown in FIG. 10. In one embodiment shown in FIGS. 10-11, the distalmost tip 202 of the microcatheter tube 185 has a sharpened conical configuration that can be formed of the plastic material of tube 185. As will be described below, it has been found that a polymeric needle and needle tip 202 is useful for its thermal characteristics in that its heat capacity will not impinge on vapor quality during vapor delivery.

FIGS. 10-11 further illustrate that the distal tip portion 108 of microcatheter tube 185 has at least one marking 204 that contrasts with the color of the microcatheter tube 185 that is adapted for viewing through lens 164 of the endoscope 118. In one embodiment, the distal tip portion has a series of annular marks 204 of a first color that contrasts with second color of tube 185, wherein the marks are not visible through the endoscope lens 164 when the microcatheter tube 185 is in the non-extended position. After the microcatheter tube 185 is extended into tissue, the marks are visible through the lens 164 which indicates the tube 185 has been extended into tissue.

Returning now to FIGS. 5 and 6, the cut-away view of the handle portion 111 shows the microcatheter member 105 and associated assemblies in the non-extended position. FIG. 5 shows flanges 208a and 208b of cocking actuator 210 are disposed on either side of actuator collar 212 that is coupled to proximal end 214 of the slidable microcatheter member 105. As can be understood from FIG. 5, the downward-extending cocking actuator 210 is adapted to cock the flanges 208a, 208b and microcatheter 105 to a cocked position which corresponds to the non-extended position of the microcatheter 105. In FIG. 5, the actuator 210 is shown in a first position B (phantom view) and second positions B' following actuation with an index finger to thus cock the microcatheter member 105 to the second releasable non-extended position (or cocked position) B' from its extended position B. The flange 208a and actuator 210 is further shown in phantom view in the released position indicated at 208a'. In FIG. 5, the flanges 208a, 208b and associated assemblies are configured for an axial travel range indicated at A that can range from about 8 mm to 15 mm which corresponds to the travel of the microcatheter 105 and generally to the tissue-penetration depth. In the embodiment of FIG. 5, the flanges 208a, 208b and microcatheter member 105 are spring-actuatable to move from the non-extended position to the extended position by means of helical spring 215 disposed around sleeve 112. As can be seen in FIG. 5, the spring 215 is disposed between the slidable flange 208b and trigger block 218 that comprises a superior portion of the release trigger 220 which is adapted to release the microcatheter 105 from its cocked position.

FIG. 5 further illustrates the release trigger 220 releasably maintaining the flange 205a and microcatheter 105 in its cocked position wherein tooth portion 222 of the trigger 220 engages the lower edge of flange 205a. It can be understood from FIG. 5 that the release trigger 220 is configured to flex or pivot around living hinge portion 224 when trigger 220 is depressed in the proximal direction by the physician's finger actuation. After actuation of trigger 220 and release of the microcatheter 105 to move distally, the axial travel of the assembly is configured to terminate softly rather than abruptly as flange 208a contacts at least one bumper element 230 as depicted in FIG. 6. The bumper elements 230 can comprise any spring or elastomeric element, and in FIG. 6 are shown as an elastomer element housed in a helical spring, which serve to cushion and dampen the end of the travel of the spring-driven microcatheter assembly. The bumper elements 230 are coupled to flange 235 which in turn is configured to be fixed between right- and left-side handle parts 125a and 125b (FIG. 4).

Now turning to the energy-delivery aspect of the system, a vapor source 250 is provided for delivering a vapor media through the microcatheter member 105 to ablate tissue. The vapor source can be a vapor generator that can deliver a vapor media, such as vapor media, that has a precisely controlled quality to provide a precise amount of thermal energy delivery, for example measured in calories per second. Descriptions of suitable vapor generators can be found in the following U.S. patent applications: application Ser. Nos. 11/329,381; 60/929,632; 61/066,396; 61/068,049; 61/068,130; 61/123,384; 61/123,412; 61/126,651; 61/126,612; 61/126,636; 61/126,620 all of which are incorporated herein by reference in their entirety. The vapor generation system also can comprise an inductive heating system similar to that described in U.S. Provisional Application Nos. 61/123,416, 61/123,417, and 61/126,647. The system further includes a controller 255 that can be set to control the various parameters of vapor delivery, for example, the controller can be set to delivery vapor media for a selected treatment interval, a selected pressure, or selected vapor quality.

Referring to FIG. 5, in one embodiment, the vapor source 250 is remote from the handle 124 and vapor media is carried to the handle by a flexible conduit 262 that couples handle and check valve 264 therein. In one embodiment, vapor can be re-circulating in conduit 262 until a solenoid in the vapor source is actuated to cause the vapor flow to thus provide an increased fluid pressure which opens the check valve 265 and allows the vapor media to flow through flexible tube 268 to valve 270 that can be finger-actuated by trigger 275. In one embodiment depicted in FIG. 5, the trigger 275 is urged toward a non-depressed position by spring 277 which corresponds to a closed position of valve 270. The trigger 275 also can be coupled by an electrical lead (not shown) to controller 255. Thus, actuating the trigger 275 can cause the controller to actuate a solenoid valve in the vapor generator to cause vapor flow through the relief valve. As a safety mechanism, the valve 270 in the handle is opened only by its actuation to thus permit the flow of vapor media through flexible tube 278 which communicates with inflow port portion 280 of collar 212 which in turn communicates with the lumen 195 in the microcatheter 105. Thus, FIG. 5 illustrates the flow path and actuation mechanisms that provide vapor flow on demand from the vapor source 250 to the vapor outlets 200 in working end 108 of the microcatheter 105.

As can be seen in FIG. 5, the handle can also provide an interlock mechanism that prevents the actuation of vapor flow if the microcatheter release trigger is in the cocked position, wherein edge portion 292 coupled to release trigger 220 can engage notch 294 in trigger 275 to prevent depression of said trigger 275.

Still referring to FIG. 5, one embodiment of the system includes a fluid irrigation source 300 that is operatively coupled to the bore 115 in extension member 112 to deliver a fluid outward from the bore 115 to the open region 162 of the probe working end 145 (see FIG. 8). As can be seen in FIG. 7, the bore 115 is dimensioned to provide a space 138 for fluid irrigation flow around the endoscope 118. In FIG. 5, it can be seen that fluid source 300, which can be a drip bag or controlled pressure source of saline or another fluid, is detachably coupled to tubing 302 in the handle which extends to a valve 305 that can be thumb-operated from actuators 308 on either side of the handle. The thumb actuator 308 also can control the rate of flow of the irrigation fluid by moving the actuator 308 progressively forward, for example, to open the valve more widely open. The fluid flows from valve 305 through tube 312 to a port or opening 315 in the extension sleeve 112 to thus enter the bore 115 of the sleeve.

FIG. 5 further depicts an aspiration source 320 operatively coupled to tubing 322 in the handle 124 which also can be actuated by valve 305 wherein the thumb actuator 308 can be rocked backwardly to allow suction forces to be applied through the valve 305 to tubing 312 that extends to port 315 in the extension member—which is the same pathway of irrigation flows. Thus, suction or aspiration forces can withdraw fluid from the working end of the device during a treatment.

Figure 13A:
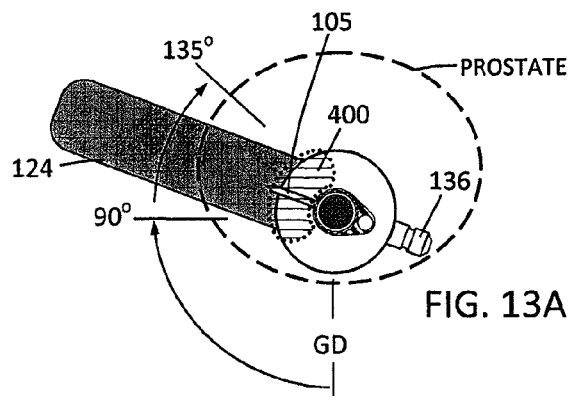
FIGS. 13A-13B are schematic views of the probe of FIG. 4 in a head-on view in a prostate indicating the radial angle of the probe as it is rotated in situ to treat lateral prostate lobes.
Figure 13B:
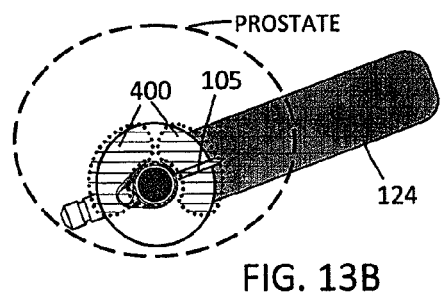

Another aspect of one embodiment of probe 100 corresponding to the invention, referring to FIGS. 4, 5, 6 and 8, is the orientation of the microcatheter or needle 105 as it exits the working end 145 relative to the orientation of the pistol grip 124 of the handle portion 111. In a method use further described below, the introducer will typically be introduced through the urethra with the pistol grip in a "grip-downward" orientation GD (FIG. 13A) with the pistol grip 126 oriented downwardly which comfortable for the physician. The treatment typically will include rotationally re-orienting the probe as indicated in FIG. 13A so that the microcatheter or needle 105 can be penetrated into prostate lobes at 90° to about 135° relative to a grip-downward position. FIGS. 13A and 13B are schematic head-on views of the probe 100 in a prostate with the microcatheter 105 deployed showing the orientation of the handle pistol grip 124, the deployed microcatheter 105 and the connector endoscope 136 which indicate the rotational orientation of the endoscope 118 and thus the orientation of the camera image on the monitor. As can be seen in FIGS. 4-6, the assembly of the introducer 110, microcatheter 105 and endoscope 118 is rotatable within the handle within flanges 235A and 235B. In one embodiment, the system has click-stops at various angles, such as every 15° between 75° and 135° relative to the grip-downward orientation GD of FIG. 13A. Thus FIGS. 13A-13A and 14A-14B depict optional methods that the surgeon may use.

FIGS. 13A and 13B depict the physician locking all components of the probe 100 in a single rotational orientation, and simply rotating his hand and pistol grip 124 to a selected orientation of greater that 90° from the grip-down position GD, then releasing the microcatheter 105 to penetrate into the prostate lobe. After actuating the vapor delivery trigger, the vapor ablates regions indicted at 400. It can be appreciated that the endoscope 118 is rotated so that the image on the monitor also is rotated. Thereafter, the physician rotates the probe as depicted in FIG. 13B to treat the other prostate lobe. This method may be preferred by physicians that are familiar with anatomical landmarks, opt for simplicity and are accustomed to viewing an image on the monitor which is rotated relative a true vertical axis of the patient anatomy.

Figure 14A:
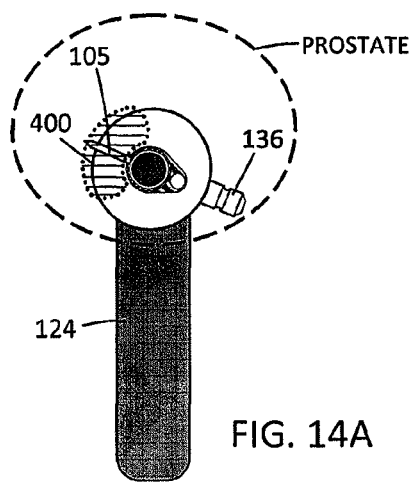
FIGS. 14A-14B are schematic views similar to that of FIGS. 13A-13B showing a method of rotating certain components of the probe again indicating the radial angles of the penetrating microcatheter of the probe of FIG. 4, while leaving the probe handle in a non-rotated position.
Figure 14B:
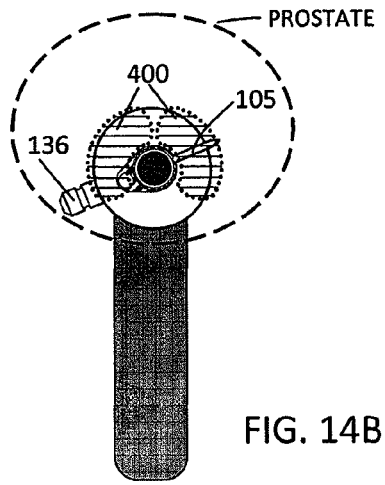

FIGS. 14A and 14B depict the physician utilizing the rotational feature of the probe and maintaining the handle pistol grip 124 in the grip-down orientation GD and rotating the introducer 110 and microcatheter 105 to the appropriate angles to treat the first and second lobes of the prostate. This method again is suited for physicians who are familiar with anatomical landmarks and are accustomed to viewing a rotated image on the monitor in the OR.

Figure 15A:
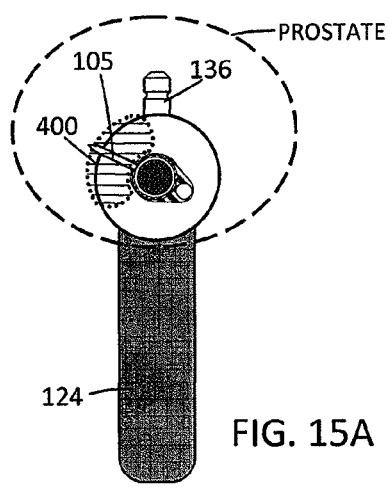
FIGS. 15A-15B are schematic views similar to that of FIGS. 13A-13B showing a method of rotating other components of the probe, again indicating the radial angles of the penetrating microcatheter in the lateral lobes of the prostate while leaving the probe handle in a non-rotated position.
Figure 15B:
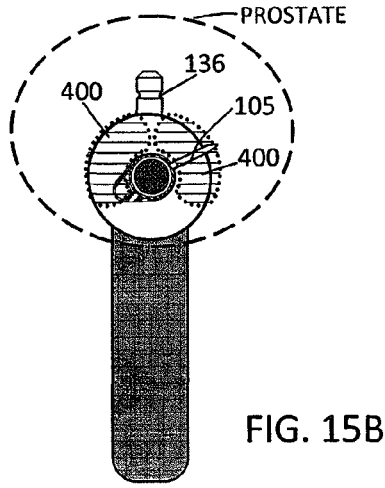

FIGS. 15A and 15B depict the physician utilizing another embodiment of a probe to treat the two prostate lobes. In the embodiment of FIGS. 5-6, it can be seen that the endoscope 118 is locked in rotational orientation with introducer 110 and the microcatheter 105—but not with the handle pistol grip. It can easily be understood that a probe can be made which allows rotational adjustment between the introducer 110 and microcatheter 105 relative to the handle pistol grip 124—but that provides a bracket that rotationally locks the endoscope 118 to the handle pistol grip 124. FIGS. 15A-15B depict the use of such an embodiment, wherein the physician can maintain the handle pistol grip 124 in the grip-down orientation GD and then rotates only the introducer 110 and microcatheter 105. In this embodiment, the image on the monitor will remain vertical instead of rotated, which may be preferred by physicians accustomed to laparoscopy in which images are not rotated on the monitor when instruments are manipulated.

In another aspect of the invention, referring to FIGS. 10-11, the microcatheter 105 carries a temperature sensor or thermocouple 405 at a distal location therein, for example as indicated in FIG. 10. The thermocouple is operatively connected to controller 255 to control vapor delivery. In one embodiment, an algorithm reads an output signal from the thermocouple 405 after initiation of vapor delivery by actuation of trigger 275, and in normal operation the thermocouple will indicate an instant rise in temperature due to the flow of vapor. In the event, the algorithm and thermocouple 405 do not indicate a typical rise in temperature upon actuation of trigger 275, then the algorithm can terminate energy delivery as it reflects a system fault that has prevented energy delivery.

In another embodiment, referring again to FIGS. 10-11, the microcatheter 105 can carry another temperature sensor or thermocouple 410 in a portion of microcatheter 105 that resides in passageway 148 of the introducer body 144. This thermocouple 410 is also operatively connected to controller 255 and vapor source 250. In one embodiment, an algorithm reads an output signal from thermocouple 410 after initiation of vapor delivery and actuation of actuator 308 that delivers an irrigation fluid from source 300 to the working end 145 of the probe. The delivery of irrigation fluid will maintain the temperature in the region of the thermocouple at a predetermined peak level which will not ablate tissue over a treatment interval, for example below 55° C., below 50° C. or below 45° C. If the temperature exceeds the predetermined peak level, the algorithm and controller can terminate vapor energy delivery. In another embodiment, a controller algorithm can modulate the rate of cooling fluid inflows based on the sensed temperature, and/or modulate the vapor flow in response to the sensed temperature. In an alternative embodiment, the thermocouple 410 can be in carried in a portion of introducer body 144 exposed to passageway 148 in which the microcatheter resides.

Method of Use

Figure 16A:
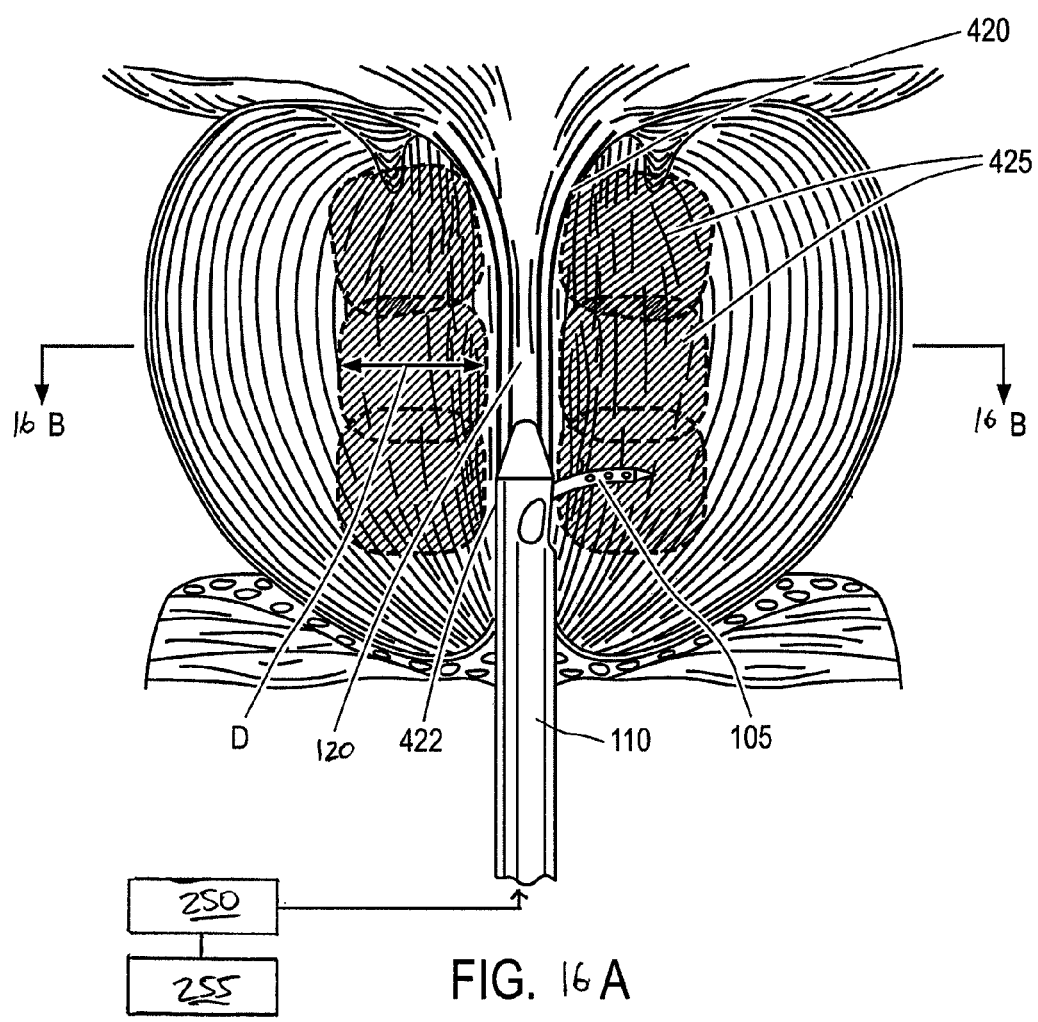
FIG. 16A is a longitudinal sectional schematic view showing a method of the invention in treating a prostate for BPH.
Figure 16B:
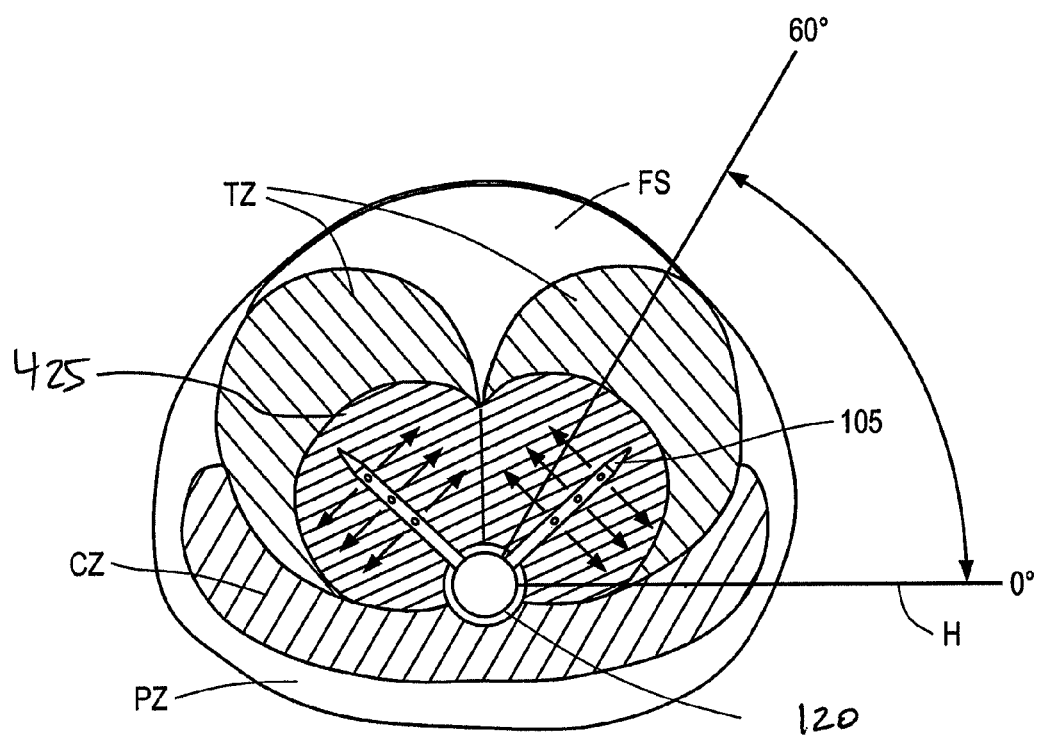
FIG. 16B is a transverse sectional view of the prostate of FIG. 16A.

Referring to FIGS. 16A and 16B, the device and method of this invention provide a precise, controlled thermal ablative treatment of tissue in the first and second lateral prostate lobes (or right- and left-side lobes), and additionally an affected median lobe in patients with an enlarged median lobe. In particular, the ablative treatment is configured to ablate stromal or smooth muscle tissue, to ablate alpha adrenergic (muscle constriction) receptors, to ablate sympathetic nerve structures, and to ablate vasculature in the treatment zone. More particularly, the method of ablative treatment is configures to target smooth muscle tissue, alpha adrenergic receptors, sympathetic nerve structures, and vasculature parallel to the prostatic urethra between the bladder neck region 420 and the verumontanum region 422 as depicted in FIGS. 16A-16B. The targeted ablation regions 425 have a depth indicated at D in FIGS. 16A-16B that is less than 2 cm from the prostatic urethra 120, or less than 1.5 cm. Depending on the length of the patient's prostatic urethra 120, the number of ablative energy deliveries can range from 2 to 4 and typically is 2 or 3.

In a method of use, the physician would first prepare the patient for trans-urethral insertion of the extension portion 110 of the probe 100. In one example, the patient can be administered a mild sedative orally or sublingually such as Valium, Lorazepam or the like from 15-60 minutes before the procedure. Of particular interest, it has been found that prostate blocks (injections) or other forms of anesthesia are not required due to lack of pain associated with an injection of a condensable vapor. The physician then actuates the needle-retraction actuator 210, for example with an index finger, to retract and cock the microcatheter 105 by axial movement of the actuator (see FIGS. 4-6). By viewing the handle 124, the physician can observe that the microcatheter 105 is cocked by the axial location of trigger 210. A safety lock mechanism (not shown) can be provided to lock the microcatheter 105 in the cocked position.

Next, the physician advances the extension portion 110 of the probe 100 trans-urethrally while viewing the probe insertion on a viewing monitor coupled to endoscope 118. After navigating beyond the verumontanum 422 to the bladder neck 420, the physician will be oriented to the anatomical landmarks. The landmarks and length of the prostatic urethra can be considered relative to a pre-operative plan based on earlier diagnostic ultrasound images or other images, such as MRI images.

Figure 17:
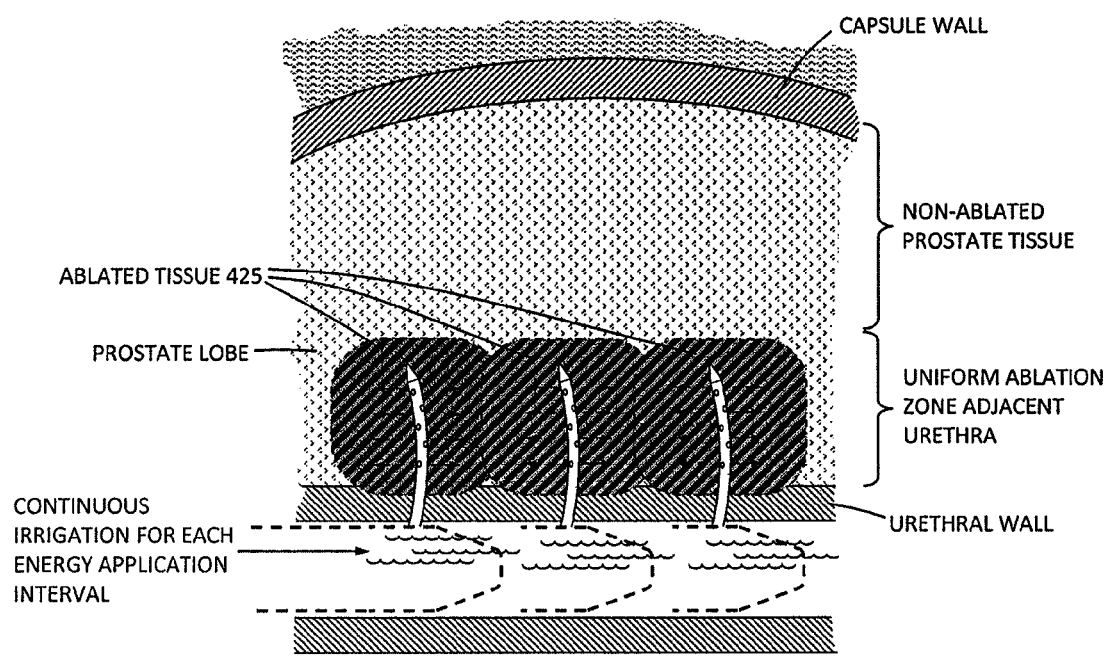
FIG. 17 is another longitudinal sectional view showing ablation zones in the method of treating a prostate for BPH.

The physician can rotate the microcatheter-carrying probe about its axis to orient the microcatheter at an angle depicted in FIG. 13A to treat a first lobe. Thereafter, the treatment included cocking and releasing the microcatheter followed by vapor delivery, the moving and repeating the vapor injection for a total of three (or more) vapor injections in each lobe. FIG. 17 is a schematic view of a method the invention wherein three penetrations of the microcatheter 105 are made sequentially in a prostate lobe and wherein energy delivery is provided by vapor energy to produce slightly overlapping ablations or lesions to ablate the smooth muscle tissue, alpha adrenergic receptors, and sympathetic nerve structures in a region parallel to the prostatic urethra. The method of the invention, when compared to prior art, reduces the burden of ablated tissue and thus lessens the overall inflammatory response leading to more rapid tissue resorption and more rapid clinical improvement.

Figure 18:
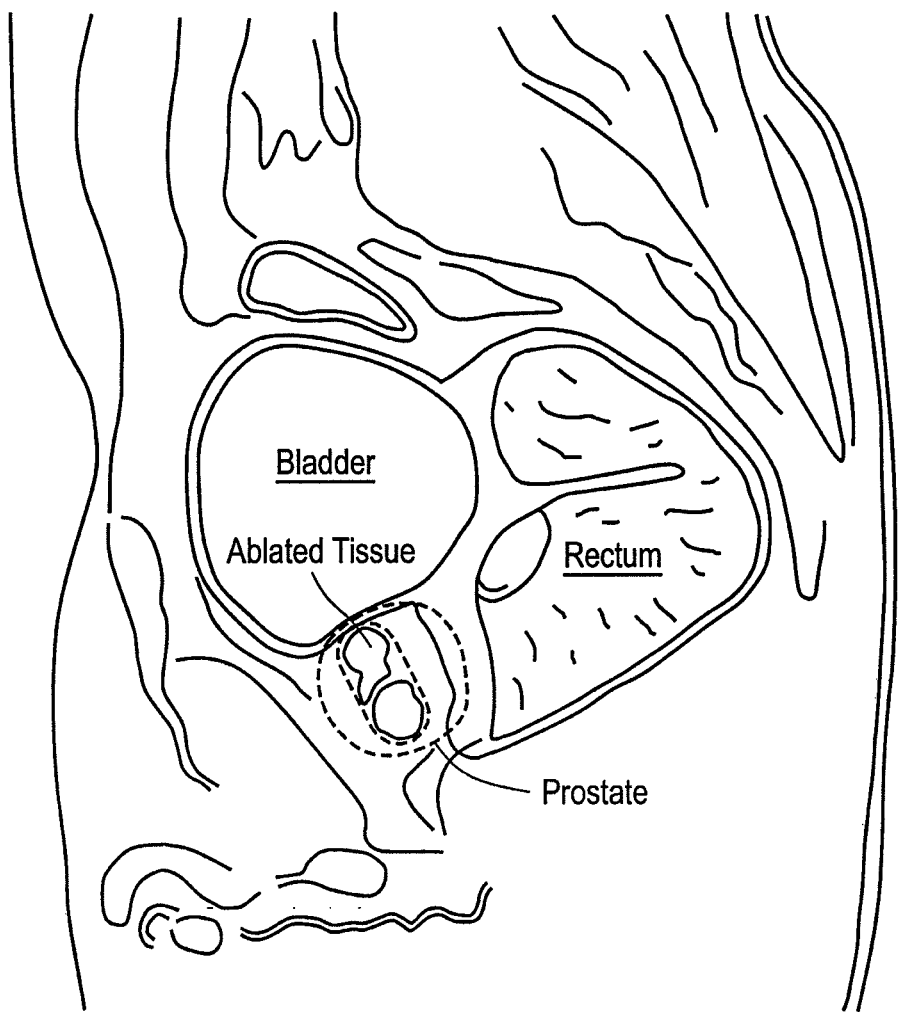
FIG. 18 is an MRI from a patient 1 week after a treatment as indicated schematically in FIGS. 16A-17.

FIG. 18 is a saggital MRI image of an exemplary BPH treatment of a patient 1 week following the procedure, in which the treatment included the following steps and energy delivery parameters. The patient's prostate weighed 44.3 grams based on ultrasound diagnosis. Amparax (Lorazepam) was administered to the patient 30 minutes before the procedure. In the treatment of the patient in FIG. 18, each treatment interval consisted of 10 seconds of vapor delivery at each of six locations (3 injections in each lobe). Thus, the total duration of actual energy delivery was 60 seconds in the right and left prostate lobes. The energy delivered was 24 cal./sec, or 240 cal. per treatment location 425 (FIG. 16A) and a total of 1,440 calories in total to create the ablation parallel to the prostatic urethra, which can be seen in the MRI of FIG. 18. In the patient relating to the MRI image of FIG. 18, the median lobe was also treated with a single 10 second injection of vapor, or 240 calories of energy. The vapor can be configured to delivery energy in the range of 5 cal./sec. to 100 cal./sec. In general, one method includes delivering less than 240 calories of energy to each site in the prostate.

Figure 3A:
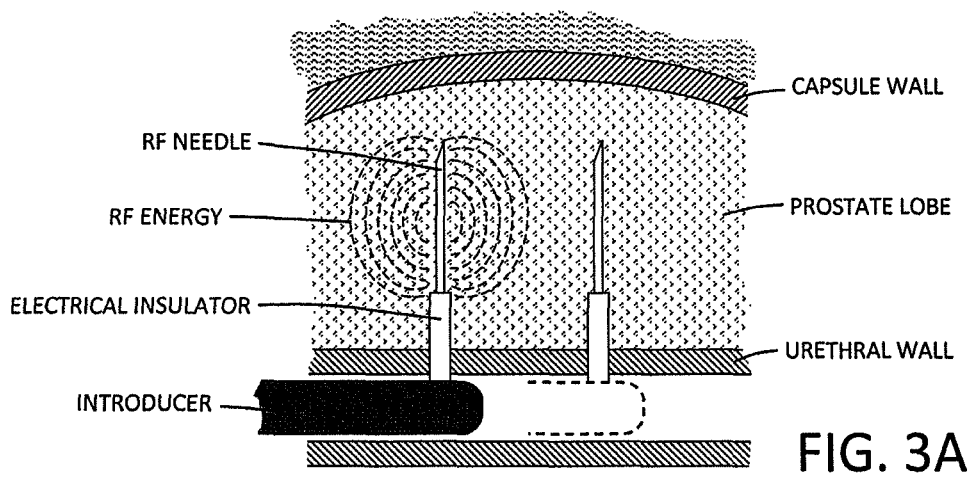
FIG. 3A is a sectional view of a normal prostate gland.
Figure 3B:
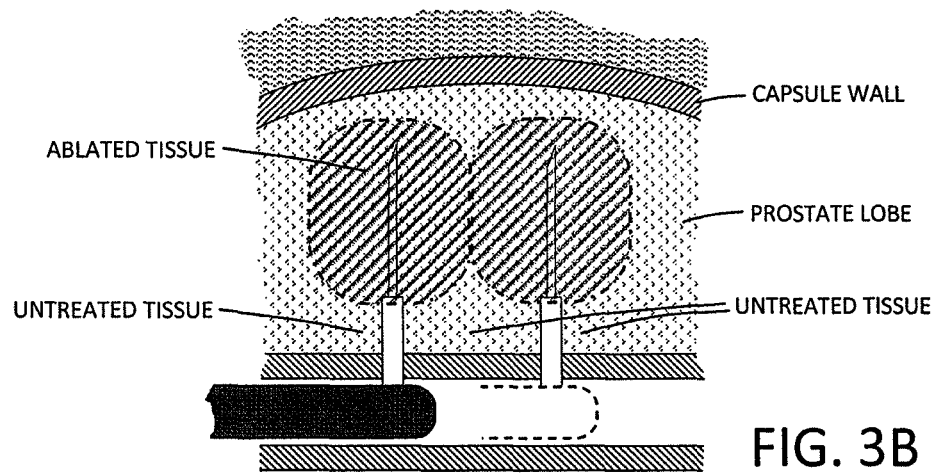
FIG. 3B is a sectional view of a prostate gland with BPH.

By comparing the method of the present invention (FIG. 17) with the prior art (FIGS. 3A-3B), it can be understood the method and apparatus of the present invention is substantially different than the prior art. FIG. 3A schematically depicts the prior art RF needle that is elongated, typically at about 20 mm in length, which ablates tissue away from the prostatic urethra and does not target tissue close to and parallel to the prostatic urethra. Second, the prior art RF energy delivery methods apply RF energy for 1 to 3 minutes or longer which allows thermal diffusion of effect to reach the capsule periphery, unlike the very short treatment intervals of the method of the present invention which greatly limit thermal diffusion. Third, the prior art RF energy delivery methods do not create a uniform ablation of tissue adjacent and parallel to the prostatic urethra to ablate smooth muscle tissue, alpha adrenergic receptors, and sympathetic nerve structures in a region parallel to the prostatic urethra.

Figure 19:
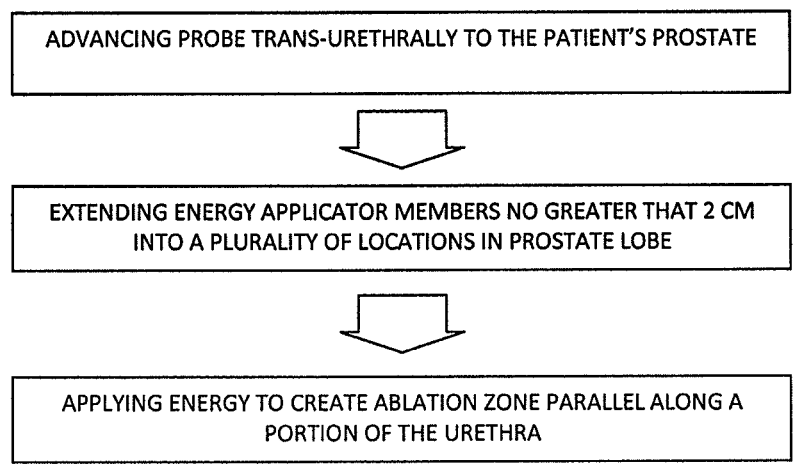
FIG. 19 is a block diagram of a method corresponding to the invention.

One method corresponding to the invention is shown in the block diagram of FIG. 19, which includes the steps of advancing a probe trans-urethrally to the patient's prostate, extending a energy applicator or microcatheter into prostate lobes in a plurality of locations to a depth of less than 2 cm, and then applying energy at each location to create an ablation zone in a continuous region parallel to at least a portion of the prostatic urethra.

Figure 20:
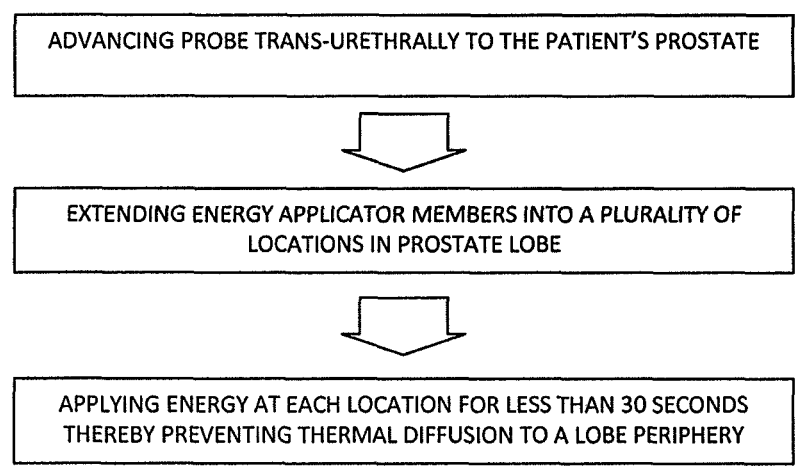
FIG. 20 is a block diagram of another method corresponding to the invention.

Another method of the invention is shown in the block diagram of FIG. 20, which includes the steps of advancing a probe trans-urethrally to the patient's prostate, extending a energy applicator or microcatheter into prostate lobes in a plurality of locations, and applying energy at each location for less than 30 seconds to thereby prevent thermal diffusion to peripheral portions of the lobes.

Figure 21:
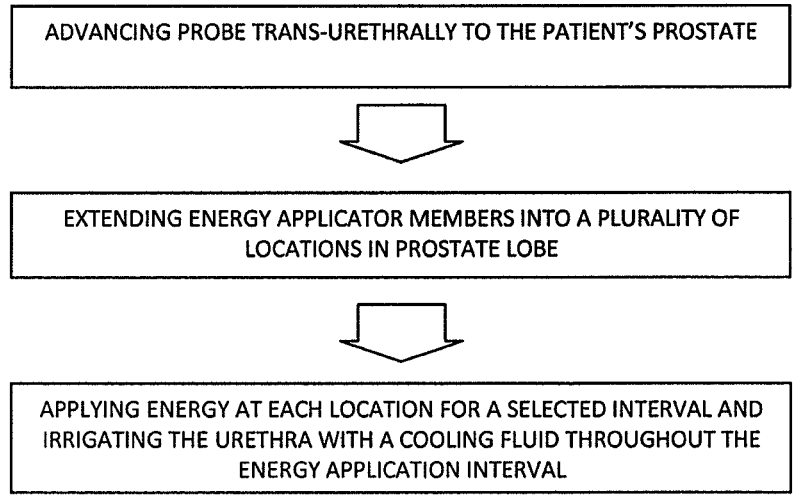
FIG. 21 is a block diagram of another method corresponding to the invention.

Another method of the invention is shown in FIG. 21, which includes the steps of advancing a probe trans-urethrally to the patient's prostate, extending a energy applicator or microcatheter into prostate lobes in a plurality of locations, and applying energy at each location for a selected interval and irrigating the urethra with a cooling fluid throughout the selected interval of energy delivery. It has been found that such a flow of cooling fluid may be useful, and most important the flow of cooling fluid can be continuous for the duration of the treatment interval since such times are short, for example 10 to 15 seconds. Such a continuous flow method can be used in prior art methods, such as RF ablation methods of FIGS. 3A-3B, since the cooling fluid volume accumulates in the patient's bladder and the long treatment intervals would result in the bladder being filled rapidly. This would lead to additional steps to withdraw the probe, remove the excess fluid and then re-start the treatment.

Figure 22:
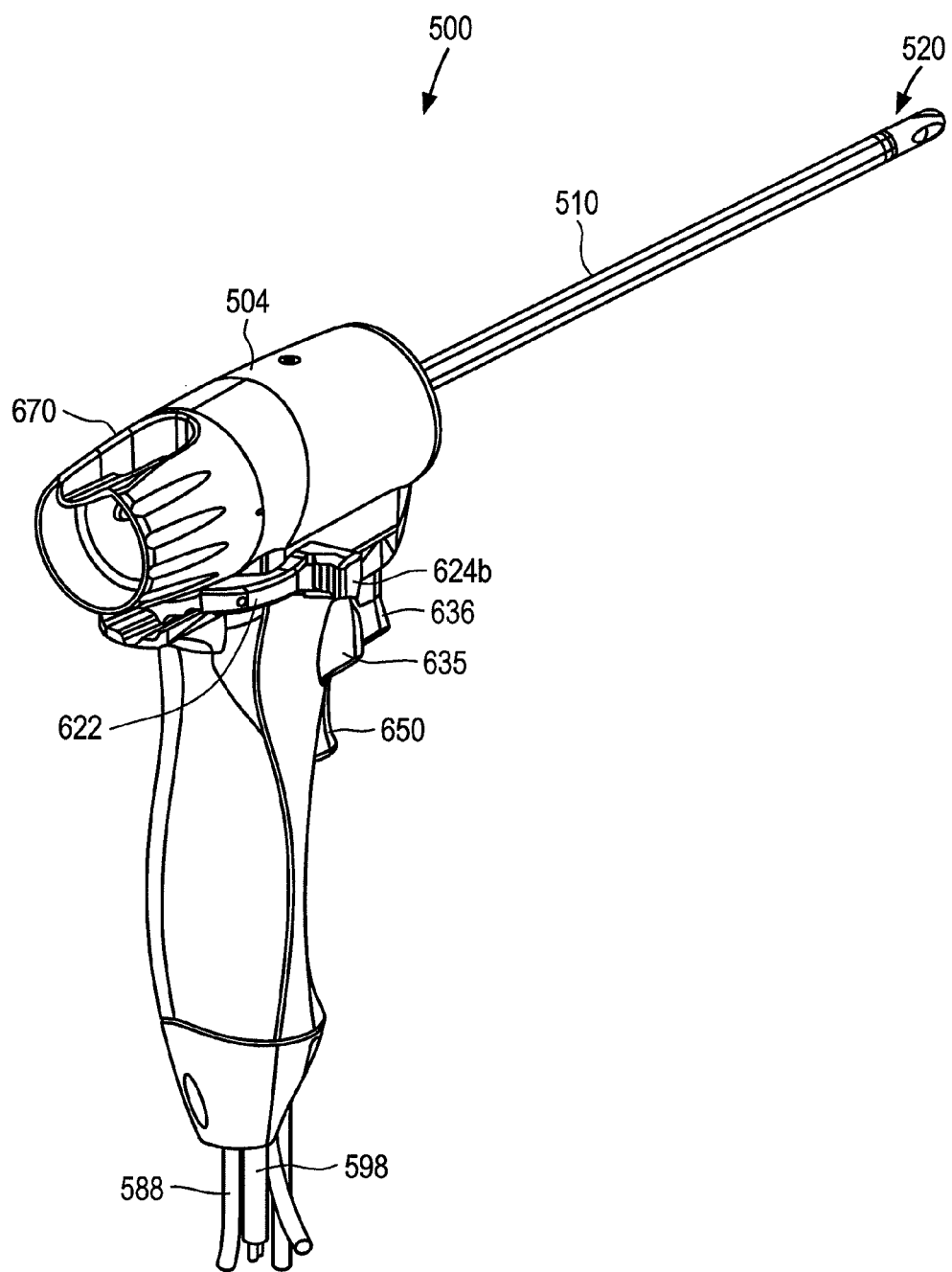
FIG. 22 is a perspective view of another embodiment of probe corresponding to invention that delivers vapor for treating BPH.
Figure 23:
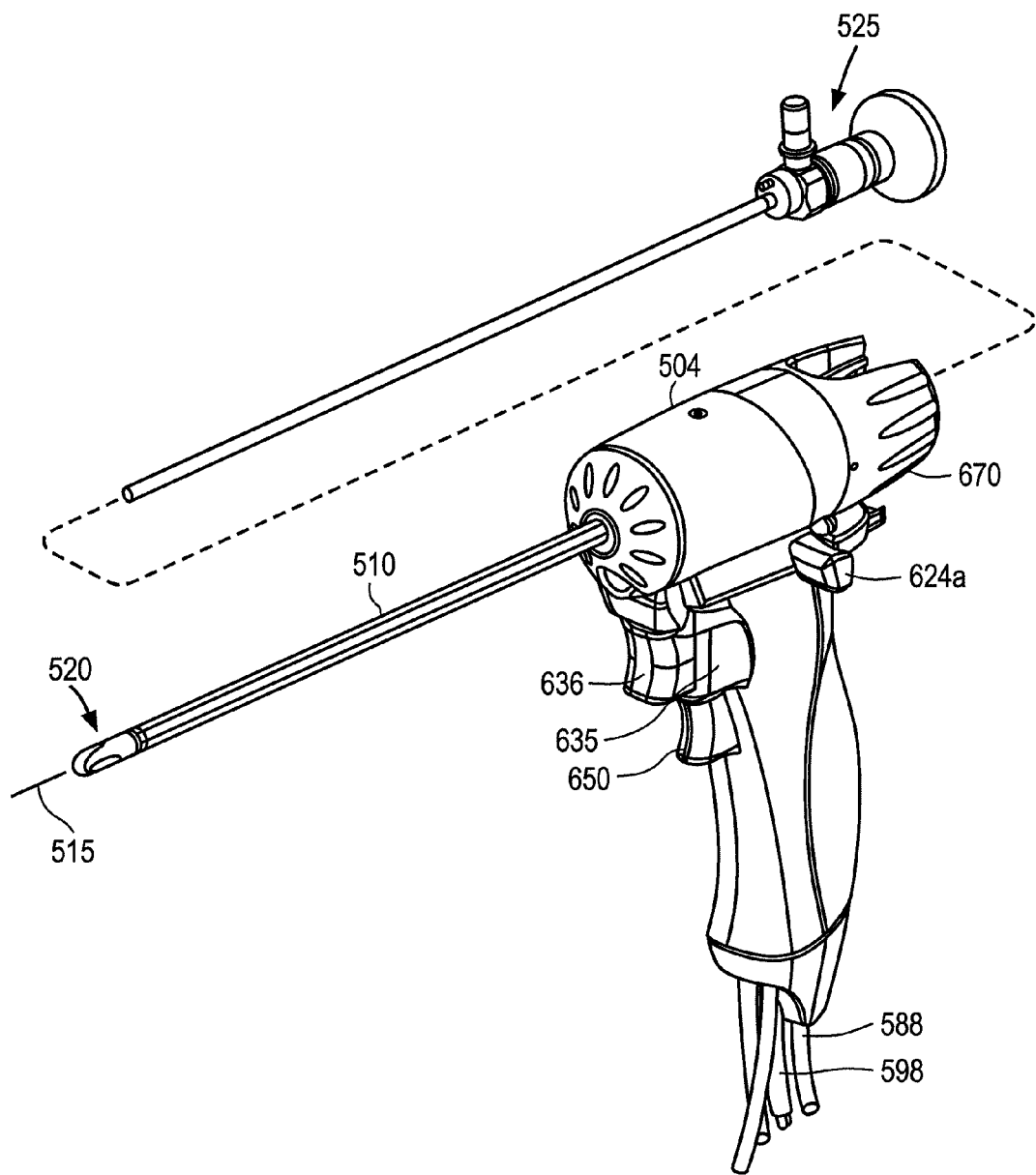
FIG. 23 is another perspective view of the probe of FIG. 22.
Figure 24:
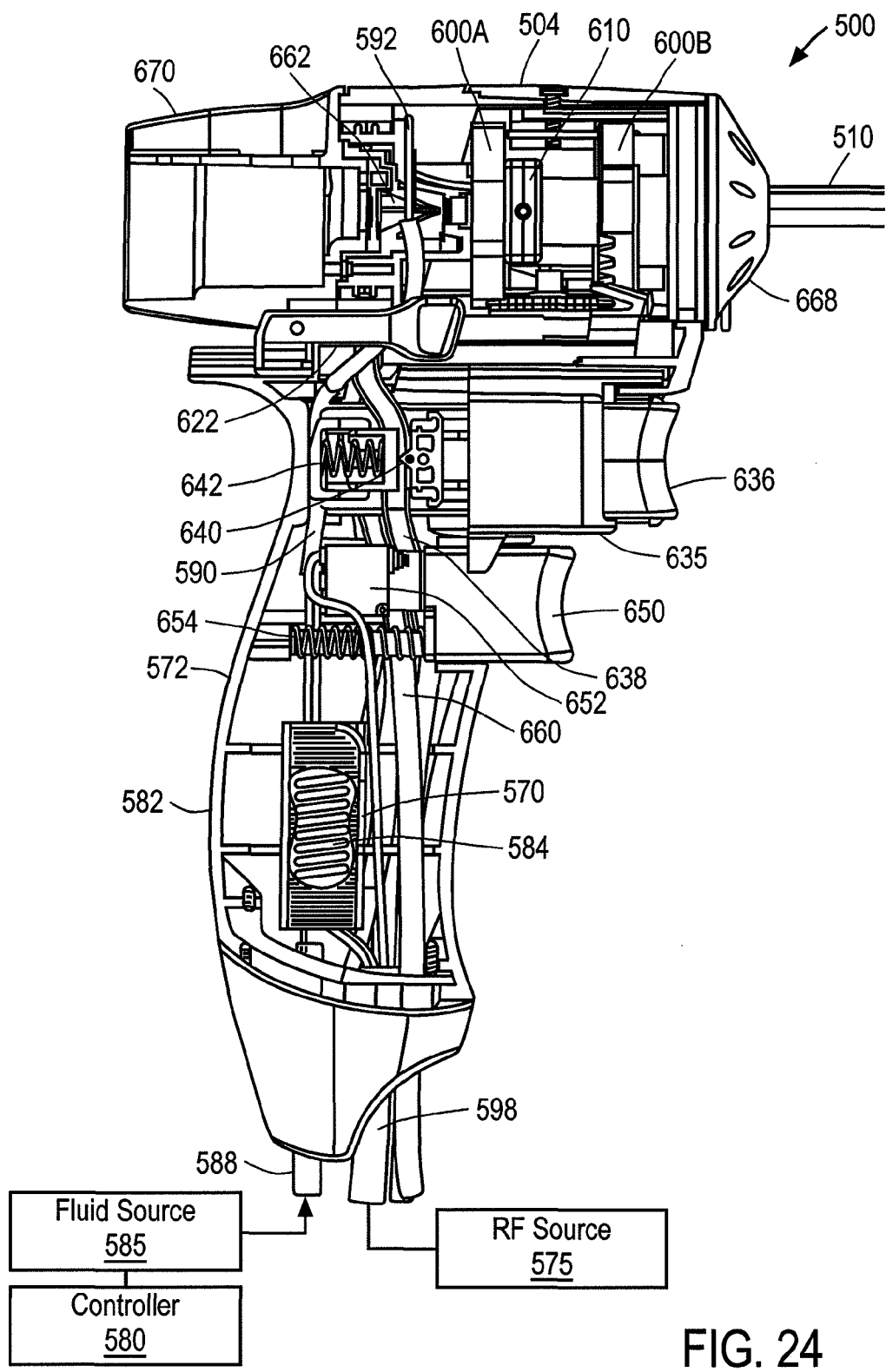
FIG. 24 is a sectional view of the handle of the probe of FIG. 22.
Figure 25:
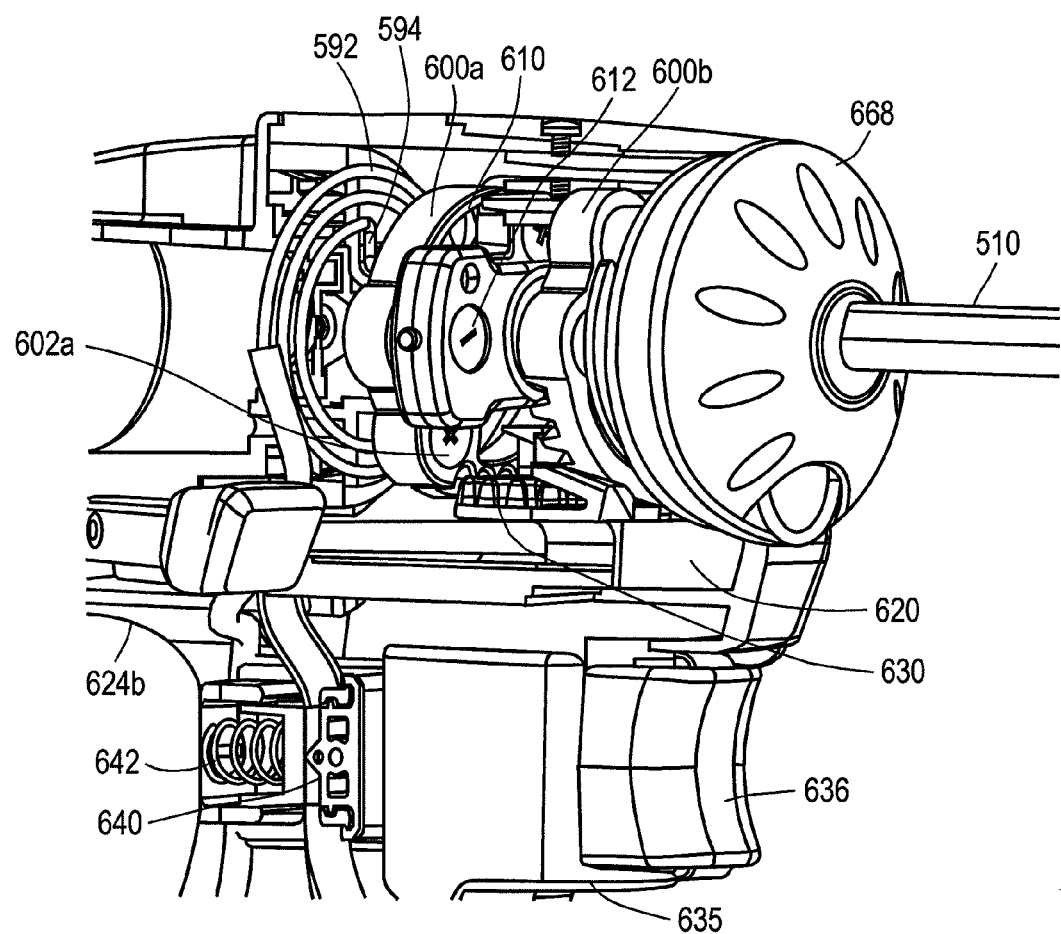
FIG. 25 is another sectional view of the handle of the probe of FIG. 22 showing components of a magnetic needle actuator system.
Figure 26:
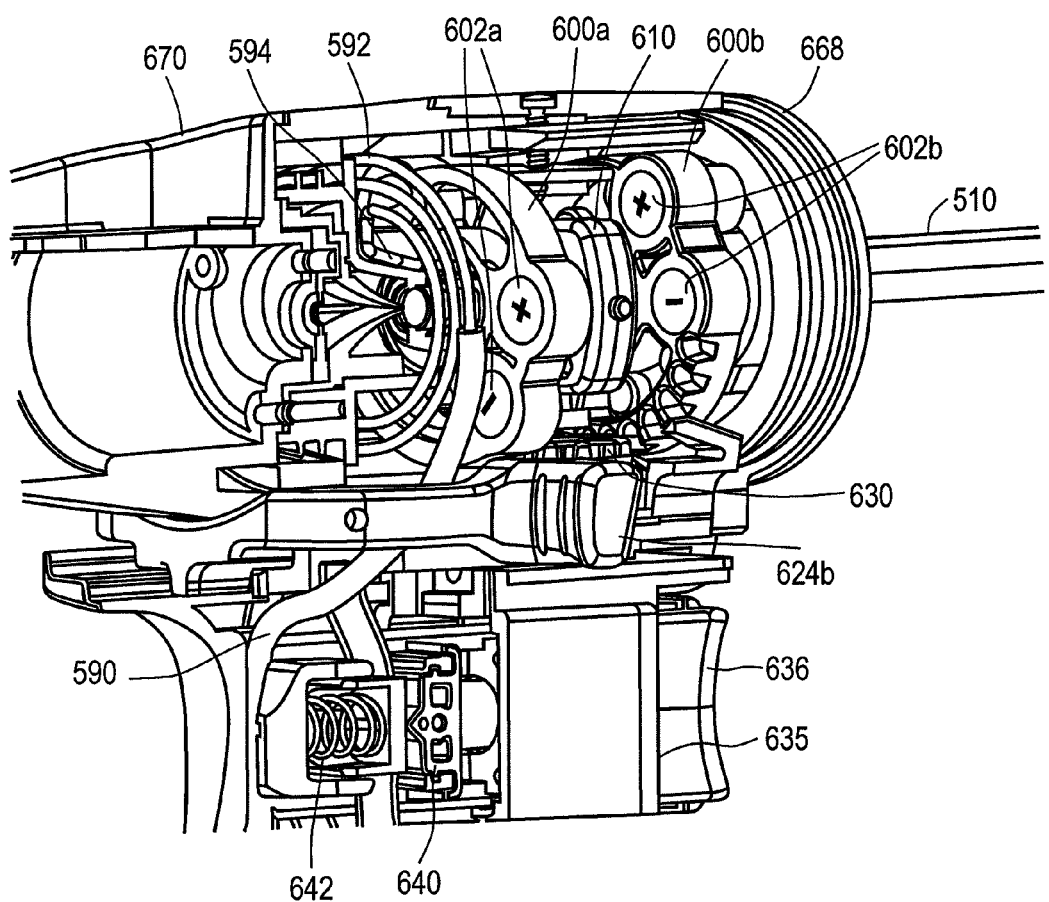
FIG. 26 is another sectional view of the handle of FIGS. 24-25 from a different angle.
Figure 27:
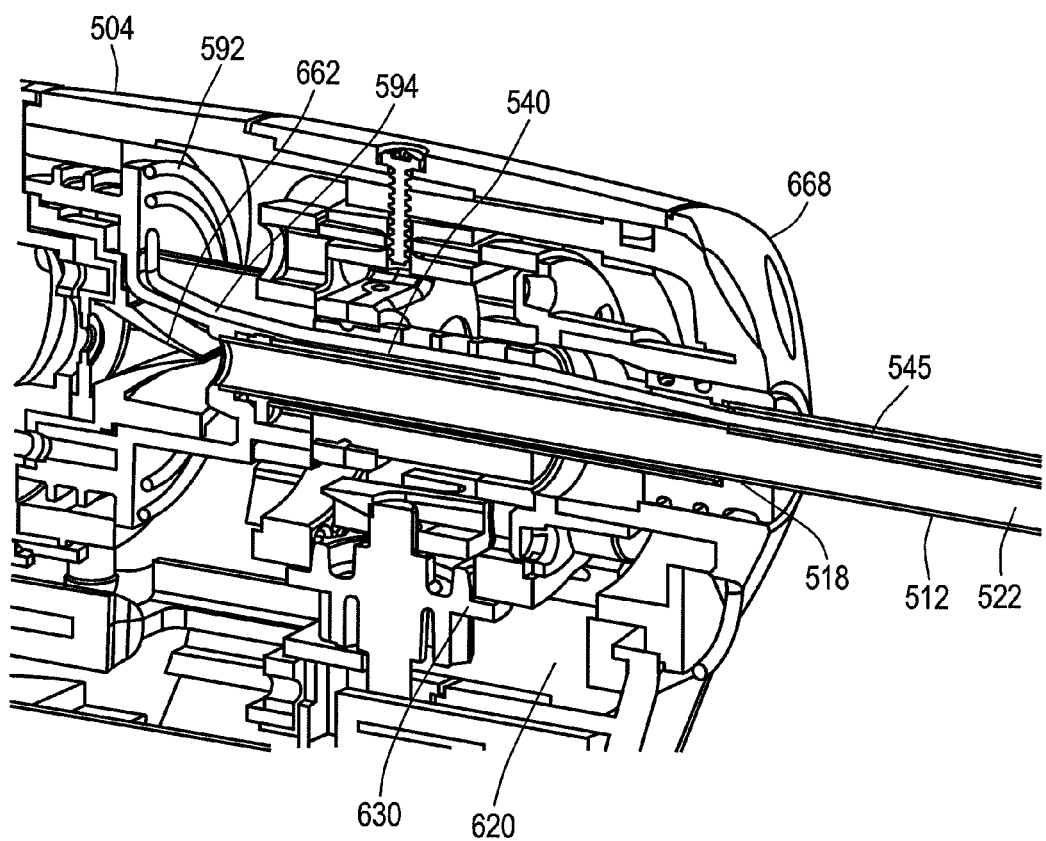
FIG. 27 is another sectional view of the handle of FIGS. 24-26 from a different angle.
Figure 28:
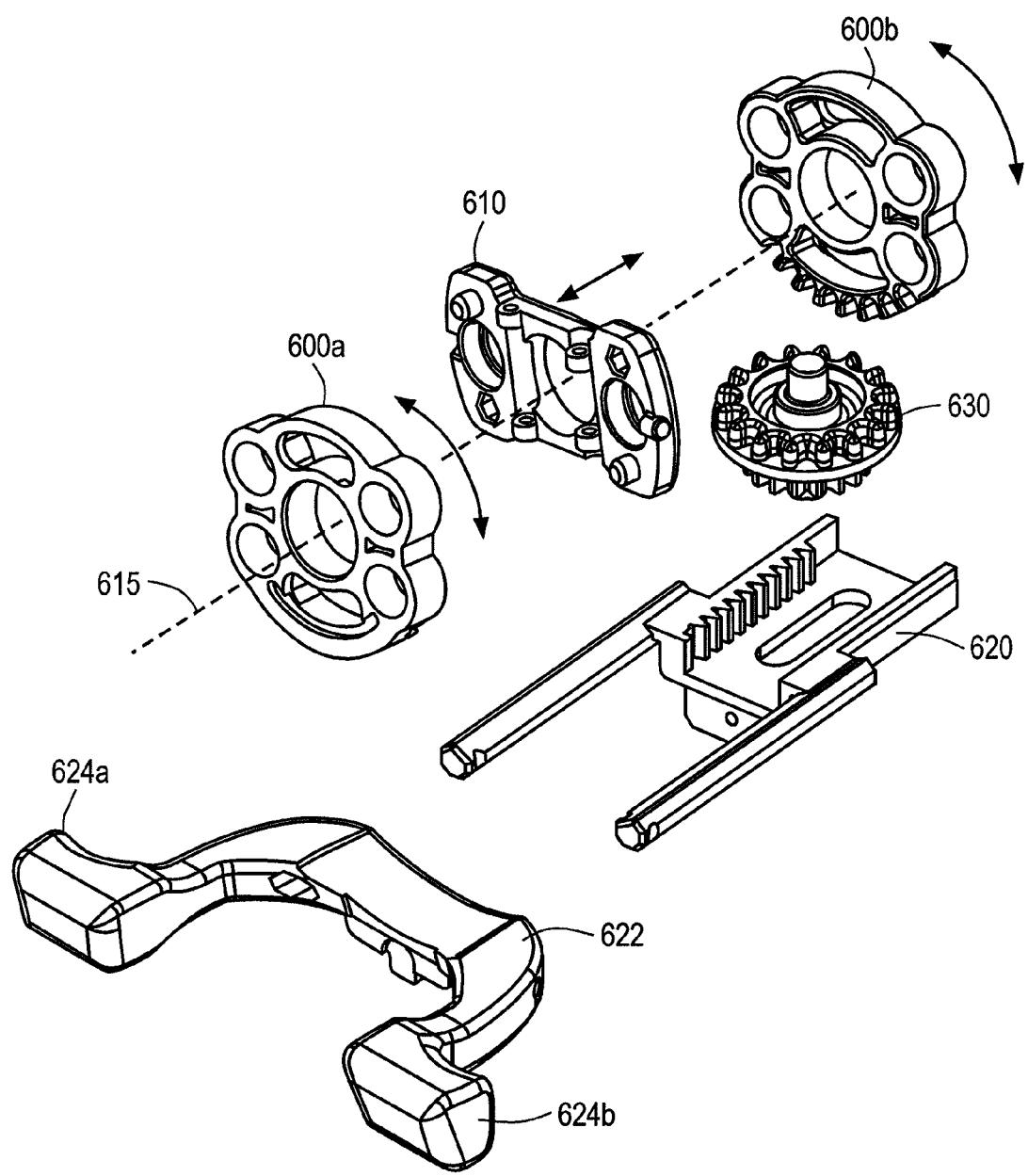
FIG. 28 is an exploded view of components of a magnetic needle actuator system as in the handle of FIGS. 24-26.
Figure 29:
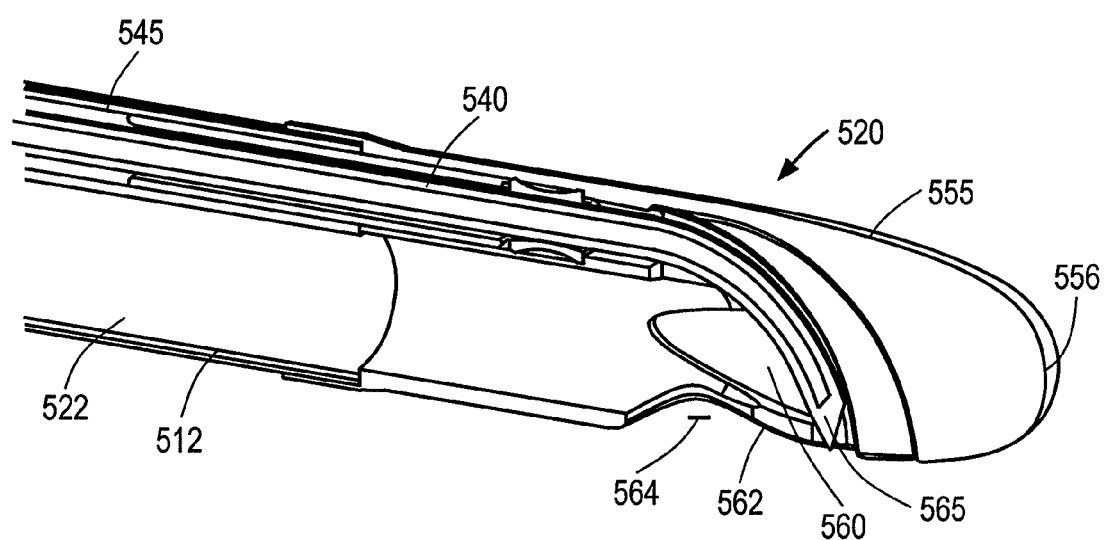
FIG. 29 is a sectional view of the distal working end of the probe of FIGS. 22-23.
Figure 30:
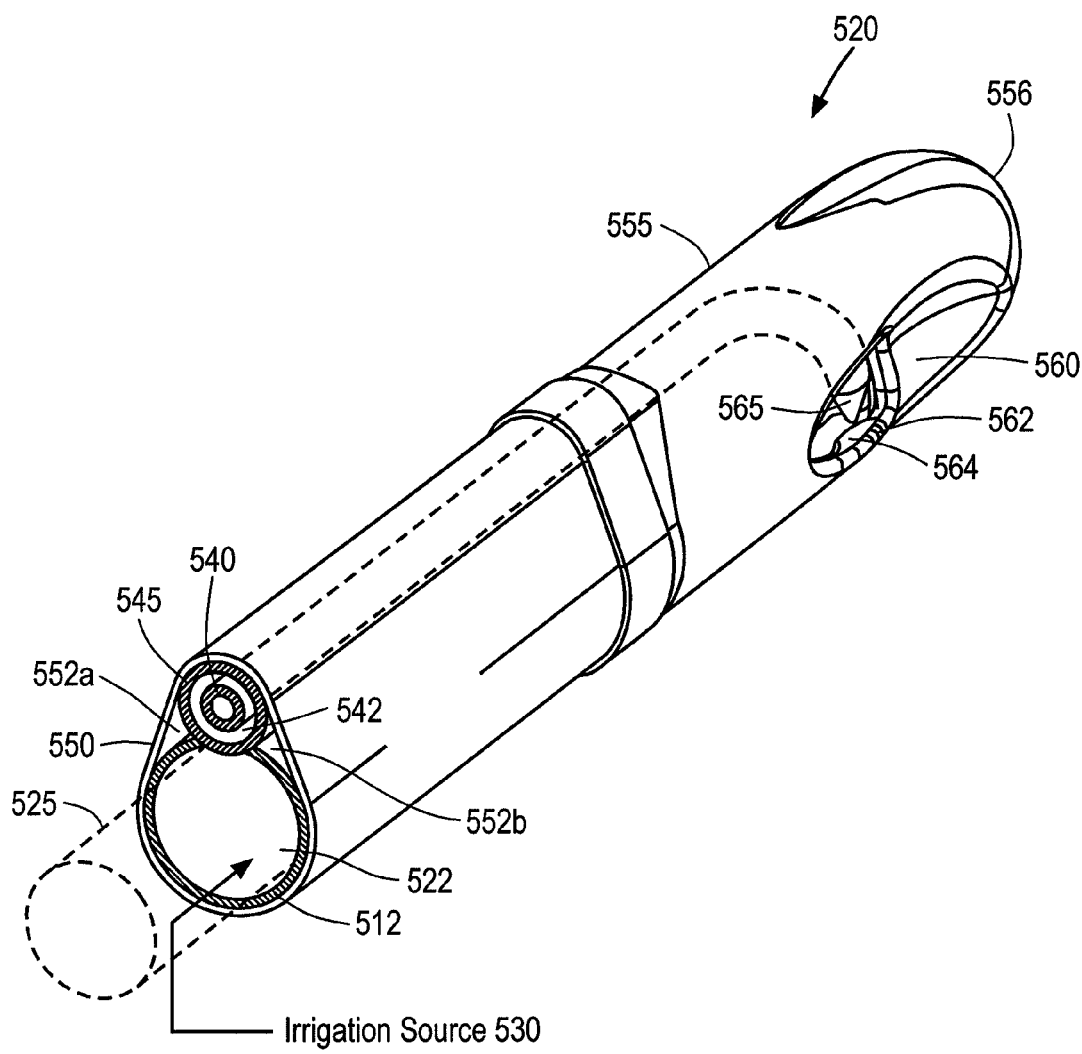
FIG. 30 is a cut-away view of the introducer portion of the probe of FIGS. 22-23.

FIGS. 22-30 illustrate another probe 500 adapted to deliver condensable vapor to prostate tissue with vapor delivery through a microcatheter or vapor delivery needle as described above. The probe 500 of FIGS. 22-30 can be configured with several different systems and mechanisms for vapor generation, vapor delivery, needle actuation, system function interlocks and for improved ergonomic function. In FIGS. 22-24, it can be seen that the probe 500 has a handle portion 504 coupled to elongate introducer portion 510 that is sized and adapted for insertion into the urethra. The introducer portion 510 can comprise a rigid introducer sleeve 512 (shown in FIGS. 27, 30) extending along longitudinal axis 515 (FIG. 23) with the introducer portion having a proximal end 518 (FIG. 27) and a distal working end 520. FIGS. 27, 29 and 30 illustrate that sleeve 512 has a lumen 522 therein that is dimensioned to receive an endoscope 525 (see FIGS. 23 and 30). An irrigation source 530 communicates with lumen 522 to provide a fluid flow around the endoscope to exit the working end 520.

In one embodiment, referring to FIGS. 27, 29 and 30, probe 500 includes an extendable-retractable microcatheter or vapor delivery needle 540 axially moveable in passageway 542 in sleeve 545 that is longitudinally coupled to sleeve 512. In some embodiments, the microcatheter or needle 540 comprises a flexible polymer tube with a sharp tissue piercing tip. In the embodiment of FIGS. 27, 29 and 30, both sleeves 512 and 545 can comprise thin-wall stainless steel tubes and can be welded together to provide a rigid structure. Referring to FIG. 30, a polymer surface layer 550 can be disposed around the assembly of sleeves 512 and 545, which in one embodiment can comprise a lubricious heat shrink material having a wall thickness ranging from 0.005" to 0.020".

As can be seen in FIG. 30, the assembly of sleeves 512, 545 and surface layer 550 can provide longitudinal air gaps 552a and 552b extending the length of sleeves 512 and 545. FIGS. 29-30 illustrate that the working end 520 of introducer portion 510 can comprise a distal body 555 of plastic or another suitable material with a blunt nose or tip 556 as described previously for advancing through the patient's urethra. The distal body 555 can be configured with side window 560 on either side of bridge elements 562 and needle window 564 as described in the previous embodiments. In FIGS. 29-30, the distal tip 565 of the microcatheter or needle 540 is shown locked in the non-extended or retracted position for when the physician is navigating the working end 520 of the probe toward a targeted site in the urethra, but which can be released from said locked position.

Now turning to FIG. 24, probe 500 can be provided with a vapor generator 570 housed with the pistol-grip portion 572 of handle 504. In some embodiments, the vapor generator can be an RF-based induction vapor generator. The vapor generator can be housed within the handle of the probe, as shown, or in other embodiments the vapor generator can be placed elsewhere within the probe or even external to the probe. The vapor generator can be coupled to an energy source, such as RF source 575 and controller 580.

In one embodiment of an RF-based vapor generator, a RF coil 582 can be positioned around a helically-wound stainless steel tubing component 584 which can be inductively heated by the RF coil 582. The water flow in the lumen of the helical stainless steel component can be converted to vapor instantly. The controller 580 can be configured to set and control all functional parameters of the probe, for example, parameters relating to vapor delivery intervals, pressure in the fluid flow into the vapor generator, vapor quality, irrigation flow rates, temperature monitoring, system cooling fans, over-ride mechanisms and the like. In FIG. 24, a fluid source 585 can be coupled to inflow line 588 for delivering a treatment fluid or media such as sterile water to the vapor generator 570. Referring to FIGS. 24-27, an outflow line 590 adapted to carry condensable vapor extends upwardly in the handle to flex-loop portion 592 that has a termination 594 that connects to a proximal end of the needle. From FIGS. 25-26, it can be understood that the flex-loop portion 592 of outflow line 590 is configured to accommodate the axial movement of the vapor delivery needle 540. Referring back to FIG. 24, the RF source 575 is coupled to RF coil 582 of the vapor generator 570 by power cord 598.

Now turning to FIGS. 24-28, the sectional and exploded views of the handle portion 504 and components therein illustrate the microcatheter or vapor delivery needle 540 and the magnetic actuator system that is adapted to move the needle in a distal or extending stroke for penetrating into tissue. The magnetic system further can be utilized to provide a proximal or retracting stroke for withdrawing the vapor delivery needle from tissue. FIGS. 26 and 28 show first and second rotatable blocks 600A and 600B that each carry magnets 602A, 602B with magnetic poles oriented as shown in FIG. 24. A central extending-retracting block 610 also carries magnets 612 (see FIG. 25) and is positioned between the first and second rotatable blocks 600A and 600B. As can be understood from FIGS. 24-26, the central block 610 is coupled to the vapor delivery needle and is configured to move distally and proximally between rotatable blocks 600A and 600B, and is keyed to not rotate, to thus extend the needle tip out of the working end 520 and to retract the needle tip back into the working end under the influence of magnetic fields. As also can be understood from FIGS. 24-26, the rotation of the first and second rotatable blocks 600A and 600B can move the magnets 602A, 602B therein (i) into a position that applies forces upon the magnets 612 in central block 610 or (ii) into a position wherein the magnets 602A, 602B will be spaced apart from magnets 612 so as to not apply force.

The magnetic actuator system can be configured to advance the vapor delivery needle a pre-determined distance. For example, when treating certain portions of prostate tissue transurethrally, the magnetic actuator system can be configured to advance the vapor delivery needle less than 2 cm from the shaft of the probe into the prostate. This pre-determined distance can be adjusted prior to therapy so as to ensure that the needle is placed directly into the proper position within the prostate.

The exploded view of several handle components in FIG. 28 illustrates a magnetic actuator subassembly. A gear rack 620 in the handle 504 is slidable proximally and/or distally when the grip body 622 is moved, for example, by the physician using his/her fingers or thumbs to engage and move axially the opposing grip elements 624a and 624b. The axial movement of the gear rack 620 then turns gear 630 which engages and rotates the first and second rotatable blocks 600A and 600B that each carry magnets 602A, 602B.

The movement of the grip 622 further cocks the central block 610 into a proximal or retracted position (FIGS. 25-26) at the same time as it rotates the first and second rotatable blocks 600A and 600B. The mechanism further has a releasable latch that locks the central block 610 and needle 540 in the retracted or non-extended position. In this position, the magnets 612 of the central block 610 are oriented directly opposed to the magnets 602A of block 600A and a maximum stored energy is provided in this temporary locked position. In FIG. 28, blocks 600A and 600B and central block 610 are shown spaced apart along longitudinal axis 615.

Needle actuation trigger 635 (FIGS. 24-26) can be actuated to release the lock or latch which then allows the stored energy and forces of the magnets 602A and 612 to extend the central block 610 and the vapor delivery needle in its distal stroke. It can be understood that the stored energy or repelling forces of magnets 602A and 612 initially drive the central block distally. Further, it can be seen in FIGS. 24-26 that the attracting forces of magnets 612 and 602B further drive the central block 610 distally. It has been found that the use of both expelling and attracting magnetic forces can provide a very high, consistent acceleration and a selected velocity over the extending stroke of the assembly. In some embodiments, the velocity of the vapor delivery needle in penetrating tissue can range from 0.1 meter per second to 20.0 meters per second.

FIGS. 24-26 show needle actuation trigger 635 and further show an integrated actuator 636 which opens and closes an inflow tubing 638 coupled to the fluid source 585. As can be seen FIGS. 24-26, a pinch valve 640 can be actuated by depressing actuator 636—wherein depressing the actuator 636 causes fluid to be provided under a selected pressure and flow rate through tubing to the endoscope lumen 522. A spring 642 urges the actuator toward the non-depressed position. FIGS. 24-26 further illustrate that needle trigger 635 and the actuator 636 are integrated to be operated with a single finger pull. Further, in one embodiment, the trigger assembly is configured to permit actuation of trigger 635 only if the irrigation actuator 636 is actuated. Thus, an interlock can be provided so that irrigation fluid will be flowing into the urethra to provide for its distension when the needle is released and penetrates into tissue.

FIG. 24 further illustrates a vapor actuator or trigger 650 located below the needle actuation trigger 635. By depressing vapor trigger 650, a electrical switch 652 is actuated which signals the controller 580 to simultaneously actuate the fluid inflow from fluid source 585 and the RF source 575 to generate vapor for a treatment interval, which can be from 1 to 20 seconds or more as described previously. A typical treatment interval can be from 5 to 12 seconds. A spring 654 urges the vapor trigger 650 toward the non-depressed position.

As also can be understood from FIG. 24, another interlock can be provided between the irrigation fluid actuator 636 and the vapor trigger 650 to insure that fluid is flowing into the urethra during the entire vapor delivery interval. This interlock can be useful to dissipate heat from sleeve 545 that houses the shaft of the vapor delivery needle 540 (see FIG. 30) and to cool and protect the surface of the urethra adjacent the targeted treatment region that is being ablated by the vapor delivery.

FIG. 24 shows that an outflow tubing 660 is provided through the handle 504 which is coupled to the endoscope lumen 522. By moving the endoscope outwardly through a duckbill seal 662, a reverse flow of fluid from the patient's bladder can occur which is important for rapidly draining a full patient bladder.

The sectional views of FIGS. 24-27 shows that the handle can comprise right and left-side mating handle parts are coupled to rotatable nose piece 668 and endoscope adapter 670 to allow independent rotation of the introducer portion 510 and/or the endoscope adapter 670 and endoscope relative to the pistol-grip handle portion 572 to provide the freedom of use illustrated in FIGS. 13A-13B, 14A-14B, and 15A-15B above.

According to the embodiments described above, a prostate treatment device can be provided comprising an introducer shaft sized and configured for transurethral access into a patient, a vapor generator configured to generate a condensable vapor, a vapor delivery needle in communication with the vapor generator and slidably disposed within the introducer shaft, and a magnetic actuator configured to apply magnetic force to the vapor delivery needle to move the vapor delivery needle between a retracted position inside the introducer shaft and an extended position at least partially outside of the introducer shaft.

In some embodiments, the magnetic actuator is configured to axially move the vapor delivery needle toward the extended position from the retracted position at a velocity ranging from 0.1 meter per second to 20.0 meters per second. In another embodiment, the vapor delivery needle can move between the retracted and extended positions (and vice versa) at a velocity ranging from 1 meter per second to 5 meters per second.

In other embodiments, the magnetic actuator is configured to cause a tip portion of the vapor delivery needle to penetrate into prostate tissue when moving toward the extended position from the retracted position. In some embodiments, the vapor delivery needle is sized and configured to extend into prostate tissue when the introducer shaft is positioned within a urethra of the patient.

In one embodiment, the magnetic actuator further comprises a first magnet carried by the vapor delivery needle, wherein the magnetic actuator is configured to move the first magnet and the vapor delivery needle proximally and distally along a longitudinal axis of the introducer shaft. In another embodiment, the magnetic actuator further comprises a second magnet carried in a frame of a handle of the device, the second magnet being configured to interact with the first magnet to move the vapor delivery needle proximally and distally along the longitudinal axis of the introducer shaft. In some embodiments, the frame is rotatable in the handle. In yet another embodiment, the magnetic actuator further comprises a third magnet carried in a second frame of the handle, the third magnet being configured to interact with the first and second magnets to move the vapor delivery needle proximally and distally along the longitudinal axis of the introducer shaft.

In some embodiments, the device can further include a grip adapted for manual control of the magnetic actuator to move the vapor delivery needle between the retracted position and the extended position. In another embodiment, the device comprises a gear rack coupled to the grip, the gear rack being configured to rotate the frame and the second magnet so as to engage or disengage from the first magnet.

In some embodiments, the device can comprise a lock configured to lock the vapor delivery needle in the retracted position. The device can further comprise a trigger adapted to release the lock to thereby move the vapor delivery needle to the extended position from the retracted position.

In one embodiment, the magnetic actuator is configured to apply a suitable magnetic force to cause the tip portion of the vapor delivery needle to withdraw from prostate tissue when moving to the retracted position. In some embodiments, the suitable magnetic force can range from 1 to 3 pounds of force during advancement and retraction. In one embodiment, the force can be at least 2 pounds of force.

In some embodiments, the device can further include a vapor actuator for actuating a flow of condensable vapor through the vapor delivery needle. The device can further comprise an interlock mechanism which permits actuation of the vapor actuator only if a releasable lock has been released.

In some embodiments, the magnetic actuator comprises at least one rare earth magnet. In other embodiments, the magnetic actuator comprises at least one neodymium or neodymium-iron-boron magnet.

In one embodiment, the magnetic actuator orients first and second magnets relative to one another to utilize repelling forces to move the vapor delivery needle along a longitudinal axis of the introducer shaft. In another embodiment, the magnetic actuator orients first and second magnets relative to one another to utilize attracting forces to move the vapor delivery needle along a longitudinal axis of the introducer shaft. In some embodiments, the magnetic actuator orients first and second magnets relative to one another to utilize attracting and repelling forces to move the vapor delivery needle along a longitudinal axis of the introducer shaft.

A method of treating prostate tissue is also provided, comprising inserting a shaft of a prostate therapy device transurethrally until a working end of the shaft is proximate to the prostate tissue, actuating a magnetic assembly to advance a vapor delivery needle from the introducer into the prostate tissue, and delivering condensable vapor from the vapor delivery needle into the prostate tissue.

In some embodiments, the condensable vapor provides a thermal effect in the prostate tissue.

In one embodiment, the vapor delivery needle advances into the prostate tissue under the influence of repelling forces between first and second magnets of the magnetic assembly. In another embodiment, the vapor delivery needle advances into the prostate tissue under the influence of attracting forces between first and second magnets of the magnetic assembly. In some embodiments, the vapor delivery needle advances into the prostate tissue under the influence of attracting and repelling forces between first and second magnets of the magnetic assembly.

A prostate treatment device is also provided, comprising an introducer shaft sized and configured for transurethral access into a patient, a vapor generator configured to generate a condensable vapor, a vapor delivery needle in communication with the vapor generator and slidably disposed within the introducer shaft, and an actuation mechanism configured to apply force to move a distal portion of the vapor delivery needle from a retracted position inside the introducer shaft to an extended position outside of the introducer shaft.

In some embodiments, the actuation mechanism moves a distal tip of the vapor delivery needle outward from the introducer shaft a distance of less than 2 cm.

In another embodiment, the device comprises a controller configured to deliver a selected volume of condensable vapor through the needle that carries less than 240 calories of energy.

In some embodiments, the actuation mechanism comprises a spring. In other embodiments, the actuation mechanism comprises at least one magnet. In one embodiment, the actuation mechanism is configured to move the vapor delivery needle toward the extended position from the retracted position at a velocity ranging from 0.1 meter per second to 20.0 meters per second.

In one embodiment, the vapor delivery needle is sized and configured to extend into prostate tissue when the introducer shaft is positioned within a urethra of the patient.

In some embodiments, the actuation mechanism comprises a first magnet carried by the vapor delivery needle. In another embodiment, the actuation mechanism comprises a second magnet carried in a frame of a handle of the device, the second magnet being configured to interact with the first magnet to move the vapor delivery needle. In some embodiments, the frame is rotatable in the handle.

In some embodiments, the device can further include a grip adapted for manual control of the magnetic actuator to move the vapor delivery needle between the retracted position and the extended position. In another embodiment, the device comprises a gear rack coupled to the grip, the gear rack being configured to rotate the frame and the second magnet so as to engage or disengage from the first magnet.

In some embodiments, the device can comprise a lock configured to lock the vapor delivery needle in the retracted position. The device can further comprise a trigger adapted to release the lock to thereby move the vapor delivery needle to the extended position from the retracted position.

In some embodiments, the device can further include a vapor actuator for actuating a flow of condensable vapor through the vapor delivery needle. The device can further comprise an interlock mechanism which permits actuation of the vapor actuator only if a releasable lock has been released.

A method of treating prostate tissue is provided, comprising inserting a shaft of a prostate therapy device transurethrally until a working end of the shaft is proximate to the prostate tissue, advancing a vapor delivery needle from the introducer into at least one site in prostate tissue to a depth of less than 2 cm, and delivering condensable vapor from the vapor delivery needle into the prostate tissue.

In some embodiments, the condensable vapor provides a thermal effect in the prostate tissue. In other embodiments, the condensable vapor delivers less than 240 calories of energy at each site.

In one embodiment, the vapor delivery needle advances into the prostate tissue under forces applied by a spring. In another embodiment, the vapor delivery needle advances into the prostate tissue under the influence of at least one magnet.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A prostate treatment device, comprising:
   an introducer shaft sized and configured for transurethral access into a patient;
   a vapor generator configured to generate a condensable vapor;
   a vapor delivery needle in communication with the vapor generator and slidably disposed within the introducer shaft; and
   a magnetic actuator configured to apply magnetic force to the vapor delivery needle to move the vapor delivery needle between a retracted position inside the introducer shaft and an extended position at least partially outside of the introducer shaft, wherein the magnetic actuator is configured to axially move the vapor delivery needle toward the extended position from the retracted position at a velocity ranging from 0.1 meter per second to 20.0 meters per second.

2. The device of claim 1 wherein the magnetic actuator is configured to cause a tip portion of the vapor delivery needle to penetrate into prostate tissue when moving toward the extended position from the retracted position.

3. The device of claim 2 wherein the magnetic actuator is configured to apply a suitable magnetic force to cause the tip portion of the vapor delivery needle to withdraw from prostate tissue when moving to the retracted position.

4. The device of claim 1 wherein the vapor delivery needle is sized and configured to extend into prostate tissue when the introducer shaft is positioned within a urethra of the patient.

5. The device of claim 1, the magnetic actuator further comprising a first magnet carried by the vapor delivery needle, wherein the magnetic actuator is configured to move the first magnet and the vapor delivery needle proximally and distally along a longitudinal axis of the introducer shaft.

6. The device of claim 5, the magnetic actuator further comprising a second magnet carried in a frame of a handle of the device, the second magnet being configured to interact with the first magnet to move the vapor delivery needle proximally and distally along the longitudinal axis of the introducer shaft.

7. The device of claim 6 wherein the frame is rotatable in the handle.

8. The device of claim 7 further comprising a grip adapted for manual control of the magnetic actuator to move the vapor delivery needle between the retracted position and the extended position.

9. The device of claim 8 further comprising a gear rack coupled to the grip, the gear rack being configured to rotate the frame and the second magnet so as to engage or disengage from the first magnet.

10. The device of claim 6, the magnetic actuator further comprising a third magnet carried in a second frame of the handle, the third magnet being configured to interact with the first and second magnets to move the vapor delivery needle proximally and distally along the longitudinal axis of the introducer shaft.

11. The device of claim 1 further comprising a lock configured to lock the vapor delivery needle in the retracted position.

12. The device of claim 11 further comprising a trigger adapted to release the lock to thereby move the vapor delivery needle to the extended position from the retracted position.

13. The device of claim 1 further comprising a vapor actuator for actuating a flow of condensable vapor through the vapor delivery needle.

14. The device of claim 13 further comprising an interlock mechanism which permits actuation of the vapor actuator only if a releasable lock has been released.

15. The device of claim 1 wherein the magnetic actuator comprises at least one rare earth magnet.

16. The device of claim 1 wherein the magnetic actuator comprises at least one neodymium-iron-boron magnet.

17. The device of claim 1 wherein the magnetic actuator orients first and second magnets relative to one another to utilize repelling forces to move the vapor delivery needle along a longitudinal axis of the introducer shaft.

18. The device of claim 1 wherein the magnetic actuator orients first and second magnets relative to one another to utilize attracting forces to move the vapor delivery needle along a longitudinal axis of the introducer shaft.

19. The device of claim 1 wherein the magnetic actuator orients first and second magnets relative to one another to utilize attracting and repelling forces to move the vapor delivery needle along a longitudinal axis of the introducer shaft.

20. A method of treating prostate tissue, comprising:
   inserting a shaft of a prostate therapy device transurethrally until a working end of the shaft is proximate to the prostate tissue;
   actuating a magnetic assembly to advance a vapor delivery needle from a retracted position in the introducer to an extended position into the prostate tissue at a velocity ranging from 0.1 meter per second to 20.0 meters per second; and
   delivering condensable vapor from the vapor delivery needle into the prostate tissue.

21. The method of claim 20 wherein the condensable vapor provides a thermal effect in the prostate tissue.

22. The method of claim 20 wherein the vapor delivery needle advances into the prostate tissue under the influence of repelling forces between first and second magnets of the magnetic assembly.

23. The method of claim 20 wherein the vapor delivery needle advances into the prostate tissue under the influence of attracting forces between first and second magnets of the magnetic assembly.

24. The method of claim 20 wherein the vapor delivery needle advances into the prostate tissue under the influence of attracting and repelling forces between first and second magnets of the magnetic assembly.

25. A prostate treatment device, comprising:
   an introducer shaft sized and configured for transurethral access into a patient;
   a vapor generator configured to generate a condensable vapor;
   a vapor delivery needle in communication with the vapor generator and slidably disposed within the introducer shaft; and
   an actuation mechanism configured to apply force to move a distal portion of the vapor delivery needle from a retracted position inside the introducer shaft to an extended position outside of the introducer shaft, wherein the actuation mechanism is configured to move the vapor delivery needle toward the extended position from the retracted position at a velocity ranging from 0.1 meter per second to 20.0 meters per second.

26. The device of claim 25 wherein the actuation mechanism moves a distal tip of the vapor delivery needle outward from the introducer shaft a distance of less than 2 cm.

27. The device of claim 25 further comprising a controller configured to deliver a selected volume of condensable vapor through the needle that carries less than 240 calories of energy.

28. The device of claim 25 wherein the actuation mechanism comprises a spring.

29. The device of claim 25 wherein the actuation mechanism comprises at least one magnet.

30. The device of claim 25 wherein the vapor delivery needle is sized and configured to extend into prostate tissue when the introducer shaft is positioned within a urethra of the patient.

31. The device of claim 29, wherein the actuation mechanism comprises a first magnet carried by the vapor delivery needle.

32. The device of claim 31, wherein the actuation mechanism comprises a second magnet carried in a frame of a handle of the device, the second magnet being configured to interact with the first magnet to move the vapor delivery needle.

33. The device of claim 32 wherein the frame is rotatable in the handle.

34. The device of claim 32 further comprising a grip adapted for manual movement of the vapor delivery needle between the retracted position and the extended position.

35. The device of claim 34 further comprising a gear rack coupled to the grip, the gear rack configured to rotate the frame and the second magnet relative to the first magnet.

36. The device of claim 25 further comprising a lock configured to lock the vapor delivery needle in the retracted position.

37. The device of claim 36 further comprising a trigger adapted to release the lock to thereby move the vapor delivery needle to the extended position from the retracted position.

38. The device of claim 25 further comprising a vapor actuator configured to actuate a flow of condensable vapor through the vapor delivery needle.

39. The device of claim 38 further comprising an interlock mechanism which permits actuation of the vapor actuator only if a releasable lock has been released.

* * * * *